United States Patent
Switek, Jr.

(10) Patent No.: US 10,429,283 B2
(45) Date of Patent: Oct. 1, 2019

(54) FRUIT TESTING DEVICE

(71) Applicant: Robert E. Switek, Jr., Pleasanton, CA (US)

(72) Inventor: Robert E. Switek, Jr., Pleasanton, CA (US)

(73) Assignee: CREATIVE VIEWPOINT MACHINERY, Pleasanton, CA (US)

( * ) Notice: Subject to any disclaimer, the term of this patent is extended or adjusted under 35 U.S.C. 154(b) by 102 days.

(21) Appl. No.: 15/411,730

(22) Filed: Jan. 20, 2017

(65) Prior Publication Data
US 2018/0209882 A1  Jul. 26, 2018

(51) Int. Cl.
| | | |
|---|---|---|
| *G01N 3/40* | (2006.01) | |
| *G01N 3/14* | (2006.01) | |
| *G01N 3/02* | (2006.01) | |
| *G01N 33/02* | (2006.01) | |

(52) U.S. Cl.
CPC ............ *G01N 3/14* (2013.01); *G01N 3/02* (2013.01); *G01N 3/40* (2013.01); *G01N 33/025* (2013.01); *G01N 2203/0003* (2013.01); *G01N 2203/0019* (2013.01); *G01N 2203/0033* (2013.01); *G01N 2203/0085* (2013.01); *G01N 2203/047* (2013.01)

(58) Field of Classification Search
CPC .. G01N 3/02; G01N 3/14; G01N 3/40; G01N 33/025; G01N 2203/0019; G01N 2203/0476; G01N 2203/0003; G01N 2203/0033; G01N 2203/0085; G01N 2203/047
USPC .......................... 73/78, 79; 173/192; 198/414
See application file for complete search history.

(56) References Cited

U.S. PATENT DOCUMENTS

| | | | |
|---|---|---|---|
| 3,470,737 A | 10/1969 | Fridley | |
| 4,061,020 A | 12/1977 | Fridley et al. | |
| 4,919,746 A * | 4/1990 | Celia | B29B 13/023 156/359 |
| 5,631,573 A * | 5/1997 | Ohno | G01R 1/0433 324/754.07 |
| 6,643,599 B1 | 11/2003 | Mohr et al. | |
| 6,788,079 B1 * | 9/2004 | Cheng | G01R 31/2887 324/750.23 |
| 7,998,669 B2 * | 8/2011 | Deppermann | G01N 1/04 435/6.1 |
| 9,500,633 B2 | 11/2016 | Mohr et al. | |

OTHER PUBLICATIONS

White, Woolf, McLeod and Burdon, "Joint Meeting of the Australian Avocado Grower's Federation and NZ Avocado Growers Association", Sep. 1997, p. 69-75.

* cited by examiner

*Primary Examiner* — Robert R Raevis
(74) *Attorney, Agent, or Firm* — Michael Petrin; Antero, Tormey, Petrin PC

(57) ABSTRACT

The invention relates generally to a mechanical device that efficiently measures physical parameters such as compression strength, elasticity, firmness, deformation resistance and the like, on one or a plurality of compressible test objects including fruits, nuts and vegetables, and which operates in a semi-automatic fashion using a rotatable turntable with multiple wells to hold a plurality of test objects in place during measurement using one or more positionable sensors capable of measuring a physical parameter when brought into contact with the test object.

20 Claims, 12 Drawing Sheets

FRUIT TESTING DEVICE

BACKGROUND

The present invention relates generally to a mechanical device that efficiently measures physical parameters such as compression strength, elasticity, firmness, deformation resistance and the like, on one or a plurality of compressible objects including fruits, nuts and vegetables and which operates in a semi-automatic fashion using an indexable turntable linked to one or a plurality of test stations capable of independently measuring said physical parameters.

More specifically, the present invention also relates to a mechanical device that employs at least one controlled free-fall test station to measure at least one of said physical parameters of a compressible object and which operates in a semi-automatic fashion using an indexable turntable to advance and test single or multiple sets of objects simultaneously using one or a plurality of test stations capable of independently measuring said physical parameters.

Various devices exist in the market to assist in testing physical properties of objects relating to the object's firmness, strength, compression resistance, elasticity and recovery from deformation, such as firmometers, penetrometers, impact testers and compression testers. Examples of firmometers and penetrometers include the Magness-Taylor pressure tester (devised in 1925) and the Effegi tester (developed recently in Italy) which make acceptance measurements but are mainly used owing to the convenience of portability due to their handheld configurations and compact size. (J. Amer. Soc. Hort. Sci. 101(6):698-700. 1976.)

Benchtop testing devices include the Instron Universal Testing Machine (available from Instron, 825 University Ave., Norwood, Mass. 02062-2643) and the Anderson firmometer (as described in the "Proceedings from the Joint Conference of the Australian Avocado Grower's Federation, Inc. and NZ Avocado Growers Association, Inc.," on 23-26 Sep. 1997. J. G. Cutting (Editor) Pages 69-75).

For certain fruit, such as cherries, testing devices have been specifically designed, such as the FirmTech1 (available from BioWorks, Inc., 31480 Hwy. K-18, Wamego, Kans. 66547, U.S.A.) The FirmTech1 device measures firmness using a force deformation mode of action. Cherries are positioned into shallow indentures on a turntable which automatically rotates to align each cherry periodically under a small load cell. A pre-determined force is progressively applied onto the cherry and the response measured by the load cell. The rate at which the force increases is defined as firmness. For a sample of cherries, average firmness, sample maximum and minimum firmness, sample standard deviation of firmness, and a frequency distribution of firmness are presented through an interfaced computer. Firmness of individual cherries in the sample can be retrieved from a file accessed through the computer. (see "Evaluation of Four Cherry Firmness Measuring Devices", Authors: Elizabeth Mitcham, Murray Clayton, Bill Biasi, and Steve Southwick, Department of Pomology, University of California, Davis, Calif. 95616, 13th Annual Postharvest Conference March 1997.) A similar device is the Soft Fruits Laboratory Turntable Firmometer available from Agrosta Sarl, 13 Rue du Bastringue 76440 Serquex, France.

However, both the Agrosta instrument and the FirmTech 1, operates by applying a progressively increasing and pre-determined force applied by use of a linear actuator or a stepper motor, which both operate by means of incremental steps produced by an electronic control module that operates to electrically pulse the actuators to advance them one step per pulse, typically a small linear distance or small rotational movement, such that a large number of pulses are typically required to move an appreciable distance. Accordingly, the applied force from these motors is produced by a series of short, fast and discreet incremental steps, which then acts to apply force to the test object or fruit piece as a series of discreet incremental force increases, which is the equivalent of a series of discreet impact events. In other words, the force applied by these current instruments is essentially equivalent to an increasing ratchet-like force, increasing incrementally in a manner that is neither smooth nor continuous in nature. Thus, any concurrent compression readings obtained from a load cell, transducer or other sensor that is being driven by a linear actuator or stepper motor necessarily suffers from the superposition of the applied, discreet increments of force applied to the object and the object's concurrent, reactive impulse to resist deformation, causing a matching series of responsive rebounds to each successive incremental pulse. Accordingly, the present means to apply force acts to introduce transient artifacts into the data stream collected during a sampling event using a stepper driven load cell to record compression and deformation resistance.

While this issue can be partially addressed by selecting linear actuators and stepper motors with high resolution capability (high number of steps per linear displacement or angular degree), the motors still operate in the same manner, so that the distortion effect is only decreased, but not eliminated. Further, the cost and size of the higher resolution motors and the electronic control modules to run them quickly become prohibitive compared to the cost of manual firmometers where one applies the force by hand or semi-automatic firmometers where force is applied using a lever.

Accordingly, what would be highly desirable is a device with means to apply a steady, continuous force during the compression test cycle rather than a series of incremental pulsed displacements, so that the collected data from a load cell, transducer or other pressure or force sensitive sensor is of much higher quality and not superimposed or contaminated with artifacts caused by the applied pulses and rebounds resulting from a stepped force application approach.

What is also desired is a device that can simultaneously measure a plurality of test objects or fruit pieces simultaneously, enabling multiple fruit pieces to be tested together. What is also desired is a device that can simultaneously measure a control object and a fruit piece to be tested together, or a first and second test of a single test object or fruit piece, and similar combinations, to be conducted either simultaneously or sequentially to calibrate the measurement systems of the device, compare calibration between the measurement systems, and to enable calibration of test measurement results obtained from testing of a control object or a fruit piece.

What is also desired is a device that does not require the use of either linear or rotational stepper motors or controllers in the mechanism of the measurement systems where they are used to directly apply force to a fruit piece or test object.

SUMMARY

Disclosed herein is a device that employs a controlled free-fall force application approach or gravity assisted means to apply compression forces to a test object or fruit piece that offers improved measurements of firmness and compressibility.

One object of the instant invention is a device for measuring the compressibility characteristics of a test object comprising (a) at least one gravity assisted measuring station comprising: (i) a riser; (ii) one or a plurality of sampling arms associated with the riser; (iii) at least one sensor element associated with each of the sampling arms; (iv) a paddle associated with the sensor element; wherein each of the sampling arms is attached to the riser in a manner that enables the sampling arm to move vertically upward in synchronicity with the upward movement of the riser; wherein the sampling arm is attached to the riser in a manner that enables the sampling arm to decouple its downward movement from the downward vertical movement of the riser following the instance of first contact of the sensor element or the paddle with a test object to be measured by the sensor element; (b) a turntable; wherein the turntable is rotationally indexable with respect to the position of the measuring station; and (c) a drive mechanism which operates to index the turntable to a position corresponding to the measuring station and which operates to raise and lower the riser during a measurement operation.

Another object of the instant invention is a device wherein the riser comprise: (i) a unit slide that operates to raise and lower the sampling arm associated with the riser; wherein an upper portion of the sampling arm supports at least one sensor element oriented in a downward sensing position; wherein the sampling arm is attached to an upper portion of the unit slide; and wherein a lower portion of the unit slide is connected to a cam follower assembly; (ii) a cam follower assembly attached to a lower portion of the unit slide; wherein the cam follower assembly operates to raise and lower the unit slide; wherein the cam follower assembly raises the unit slide in a first upward vertical direction to a maximum height corresponding to a top of cam position and then further operates to lower the unit slide in a second downward vertical direction to an intermediate measuring position corresponding to a test position that operates to bring the sensor element into contact with a test object positioned on the turntable in order to measure the compressibility of the test object, and then further operates to allow the paddle associated with the sensor element to compress the test object by means of gravitational force until the unit slide achieves a lowermost final position as determined by the degree of compression of the test object as measured between an initial uncompressed state and a final compressed state.

A further object of the instant invention is a device wherein the cam follower assembly comprises: (i) a cam follower plate that is attached to a lower portion of one or a plurality of the risers; (ii) a cam follower; and (iii) a cam follower shaft; wherein the cam follower has a proximal side that is attached to the cam follower plate and an opposite distal side that is attached to the cam follower shaft; wherein the cam follower operates to convert the rotational motion of a three dimensional cylindrical cam into a linear vertical motion with a first maximum vertical position corresponding to the top of cam position and to a second intermediate lower vertical position corresponding to the start of test position sequentially during one rotation of the three dimensional cylindrical cam; wherein the three dimensional cylindrical cam has a grooved cam surface featuring a continuous cam channel located on the three dimensional cylindrical cam's outer surface of rotation that couples with the cam follower; and wherein the cam follower is attached to the cam follower shaft and guides the cam follower shaft during rotation of the three dimensional cylindrical cam about a vertically oriented axis of rotation of the three dimensional cylindrical cam.

Another object of the instant invention is a device wherein the turntable has a plurality of shallow sample wells located on the upper surface of the turntable; wherein the sample wells are each configured to receive and hold one test object in a stationary position with respect to the sample well; and wherein the sample wells are positioned radially equidistant about the center axis of rotation of the turntable; and wherein the turntable is rotationally indexable and operates to position at least one test object held within a sample well under at least on measuring station.

Yet another object of the instant invention is further comprising a second measuring station comprising a second riser, a second sampling arm, a second sensor element and a second paddle associated with the second sensor element; wherein the turntable is rotationally indexable and operates to position at least two separate test objects held within at least two adjacent sample wells, a first sample well and a second sample well, in alignment with the first and the second measuring station, respectively, prior to a measurement operation.

Another object of the instant invention is a device wherein the drive mechanism operates to drive the rotation of a Geneva turntable indexing wheel that comprises a plurality of Geneva drive indents and a plurality of Geneva blocking stop indents; wherein the Geneva drive indents are configured to engage a Geneva driving pin located on the Geneva drive pulley that operates to rotationally index the turntable between a loading position and a first measuring position; wherein the loading position is selected from a position located immediately adjacent to the first measuring position located under a first measuring station; and wherein the first measuring position corresponds to a first set of one or plurality of positions that correspond to positions of sample wells located on the surface of the turntable with test objects present that are aligned with and located immediately under one or a plurality of measuring stations when the turntable is rotated into the first measuring position; wherein the Geneva drive indents are configured so as to decouple from the Geneva driving pin and prevent the further rotation of the turntable during a first measurement cycle; and wherein the Geneva drive indents further operate to engage the Geneva driving pin to index the turntable to a second and subsequent plurality of measuring positions wherein an additional one or plurality of test objects present are then subsequently aligned with and located immediately under the measuring stations during the second and the subsequent measurement operations.

Yet another object of the instant invention is a device wherein the Geneva driving pin on the Geneva drive pulley is configured to engage with a first Geneva drive indent at a first position and which operates to rotationally index the turntable to a second position whereby the Geneva driving pin decouples from the first Geneva drive indent, and remains decoupled until the Geneva drive pulley is rotated to a third position whereby the Geneva driving pin couples with a second and adjacent Geneva drive indent, corresponding to the end of a first measurement operation; and wherein the Geneva driving pulley operates to rotate the three dimensional cylindrical cam one complete rotation about its axis during any one of the measurement operations; wherein the three dimensional cylindrical cam operates to drive the cam follower along the cam follower groove located on the grooved cam surface of the three dimensional cylindrical cam.

Another object of the instant invention is a device wherein the drive mechanism drives the rotation of a Geneva blocking disc; wherein the drive mechanism is coupled to the Geneva turntable indexing wheel by means of the Geneva drive pulley driven by a keyed drive shaft; wherein the Geneva blocking disc mates with the Geneva blocking stop indents when they are brought into rotational alignment and which operates to prevent the rotation of the turntable during any one of the measurement operations; and wherein the Geneva blocking disc is located at the proximal end of the keyed drive shaft and is in a plane coincident to a plane passing through the Geneva turntable indexing wheel and perpendicular to a vertical axis passing through the long axis of the keyed drive shaft.

Another object of the instant invention is a device wherein an upper surface of the three dimensional cylindrical cam is axially connected to and operates to rotate in synchronicity with the Geneva drive pulley; wherein the Geneva drive pulley is coupled to a gear motor pulley by a suitable mechanical linkage that enables the gear motor to turn the Geneva drive pulley; and wherein the mechanical linkage is selected from a ball chain, belt, link chain, clutch, wire, gear system, slip clutch, and combinations thereof.

A further object of the instant invention is a device wherein the three dimensional cylindrical cam is axially connected to the Geneva drive pulley by means of keyed drive shaft whose proximal end is supported by a set of upper drive shaft bearings and whose distal end is supported by a set of lower drive shaft bearings; wherein the upper and lower drive shaft bearings and the gear motor are optionally contained within a drive bearing housing; wherein the proximal end of the keyed drive shaft couples to the lower engagement surface of the Geneva drive pulley that bears the Geneva driving pin on an opposite or upper engagement surface of the Geneva drive pulley; wherein the Geneva driving pin extends upwardly and into the plane of rotation of the Geneva turntable indexing wheel and operates to engage with the Geneva drive indents located on the outer peripheral edge of the Geneva turntable indexing wheel; and which further operates to couple with the Geneva turntable indexing wheel when the Geneva drive pulley is in a position corresponding to any one of a plurality of rotational positions corresponding to the start of a measurement operation; and wherein the Geneva drive pulley operates to rotate the three dimensional cam which in turn operates to raise and lower one or a plurality of the risers bearing the sampling arms.

Yet another object of the instant invention is a device wherein the one or a plurality of sampling arms further comprises a sensor unit connected to the sampling arm and oriented in a downward direction for sensing compressive forces exerted by the sampling arm against a test object located within a sample well and positioned in coaxial alignment with the test object located within the sample well on the surface of the turntable; wherein the sensor unit optionally bears a paddle on its lowermost surface wherein the paddle has a contact surface that operates to contact the test object and further operates to distribute the weight of the sampling arm uniformly across the contact surface of the paddle when in contact with the test object; wherein the paddle operates to transmit the compressive forces between the test object and the sensor unit.

Another object of the instant invention is a device wherein the first and second riser comprise a first unit slide and a second unit slide; wherein the first and second unit slide are connected on their respective lower ends to the proximal side of a first slide carriage plate and a second slide carriage plate, respectively; wherein the first and second slide carriage plates are coupled on their distal sides to a proximal side of the cam follower plate; wherein the cam follower plate bears the cam follower shaft on it distal side; wherein the distal side of the cam follower plate is connected to an encoder slide assembly; wherein the encoder slide assembly comprises an encoder assembly top plate, an encoder assembly side plate to which the encoder unit is attached; and a riser encoder mounting flange that connects to the cam follower plate to provide a reference vertical displacement scale against which the instantaneous vertical position of the encoder slide can be measured.

Another object of the instant invention is a device wherein the first and the second risers operate to travel vertically within a first unit slide and a second unit slide, respectively, driven vertically by means of the cam follower plate; wherein the first and second unit slides bear a plurality of slide vee rollers that engage with a plurality of slide vee guides located within the respective unit slide grooves of the first and second unit slides; wherein the slide vee rollers engage the slide vee guides to enable the vertical movement of the risers from a lowermost vertical position defined as the bottom of cam range to an uppermost vertical position defined as the top of cam range; and wherein a set of first and second slide mount limit screws located at the bottom of their respective first and second unit slides and which operate to arrest any further downward vertical movement of the first and second unit slides beyond the lowermost vertical position corresponding to the bottom of cam range.

Yet a further object of the instant invention is a device wherein the encoder slide assembly comprises an encoder slide carriage, an encoder slide and an encoder mount block; wherein the encoder slide operates to travel vertically within the encoder slide carriage when vertically driven by the cam follower plate; and wherein a linear encoder is mounted to one side of the encoder mount block and operates to generate an electronic signal that is proportional to the instantaneous vertical position of the linear encoder with respect to its subsequent vertical displacement from an initial set position corresponding to the bottom of cam range.

Yet another object of the invention is a device further comprising a power supply, a computer processing unit, an input unit, a display unit, a motor, at least one linear encoder, a first and second sensor element; and optionally a motor controller unit and data storage unit; wherein the input and display units are selected from a cathode ray tube (CRT) computer, laptop, tablet computing device, digital or analog display unit, cellular communications device and combinations thereof; wherein the first and second sensor elements generate electronic signals that are received and analyzed by the computer processing unit; wherein the computer processing unit controls the motor and the motor control unit to raise and lower the first and second sampling arms and to rotate the turntable for the purpose of measuring the compressibility of test objects located within sampling wells on the upper surface of the turntable; and wherein the computer processing unit controls the indexing of the turntable by means of the motor controller unit between a first testing position and a subsequent second testing position whereby a compression test of a first set and subsequent additional set of test objects can be completed automatically without user intervention after the loading of the plurality of test objects into the plurality of sampling wells has been completed prior to starting the compression test.

One additional object of the instant invention regarding the inventive device is a method for measuring the compressibility of one or more test objects in a repeated series of steps defining a complete test cycle using a device comprising: (a) at least one gravity assisted measuring station comprising: (i) a riser; (ii) one or a plurality of sampling arms associated with the riser; (iii) at least one sensor element associated with each of the sampling arms; (iv) a paddle associated with the sensor element; wherein each of the sampling arms is attached to the riser in a manner that enables the sampling arm to move upward in synchronicity with the upward movement of the riser; and wherein the sampling arm is attached to the riser in a manner that enables the sampling arm to decouple its downward movement from the downward movement of the riser following the instance of first contact of the sensor element or the paddle with the test object to be measured by the sensor element; (b) a turntable; wherein the turntable has a plurality of sample wells and is rotationally indexable with respect to the position of the measuring station; and (c) a drive mechanism which operates to index the turntable to a position corresponding to the measuring station and which operates to raise and lower the riser; wherein the steps comprise: (A) enabling the drive mechanism to simultaneously raise the sampling arms to permit the loading of test objects to be measured in a first and subsequent plurality of sets of the sample wells located on the upper surface of the turntable; (B) enabling the drive mechanism to then lower the sampling arms by means of the risers in order to bring the plurality of sensor elements with attached paddles into contact with a first set of the test objects for the purpose of measuring the degree of compression of a the first set of test objects independently in a first measurement operation; (C) collecting electronic data generated by the sensor elements during the first measurement operation; (D) enabling the drive mechanism to simultaneous raise the sampling arms and to rotationally index the turntable to a subsequent test position wherein a new set of test objects in a second set of sample wells are located under the sampling arms; (E) repeating steps B, C and D in this order for each unmeasured set of test objects to be tested, and repeating these steps until the last set of test objects have been measured in a final measurement operation representing the end of a complete test cycle; and (F) enabling the drive mechanism to raise the sampling arms and rotationally index the turntable to a final position wherein all the test objects can be removed from their respective sample wells on the turntable.

One additional object of the invention is a method of using the inventive device which further comprising a power supply, a computer processing unit, an input unit, a display unit, a motor, at least one linear encoder, a first and second sensor elements; and optionally a motor controller unit and data storage unit; wherein the linear encoder provides an output corresponding to the instantaneous relative vertical position of the linear encoder with respect to the position of the first and second sampling arms and their respective first and second sensor elements during each testing operation so as to enable the compression force applied to each test object to be independently measured and recorded during a test cycle of a plurality of differently sized test objects each located on its own sample well on the surface of the turntable.

DESCRIPTION

Generality of Invention

Figure 1:
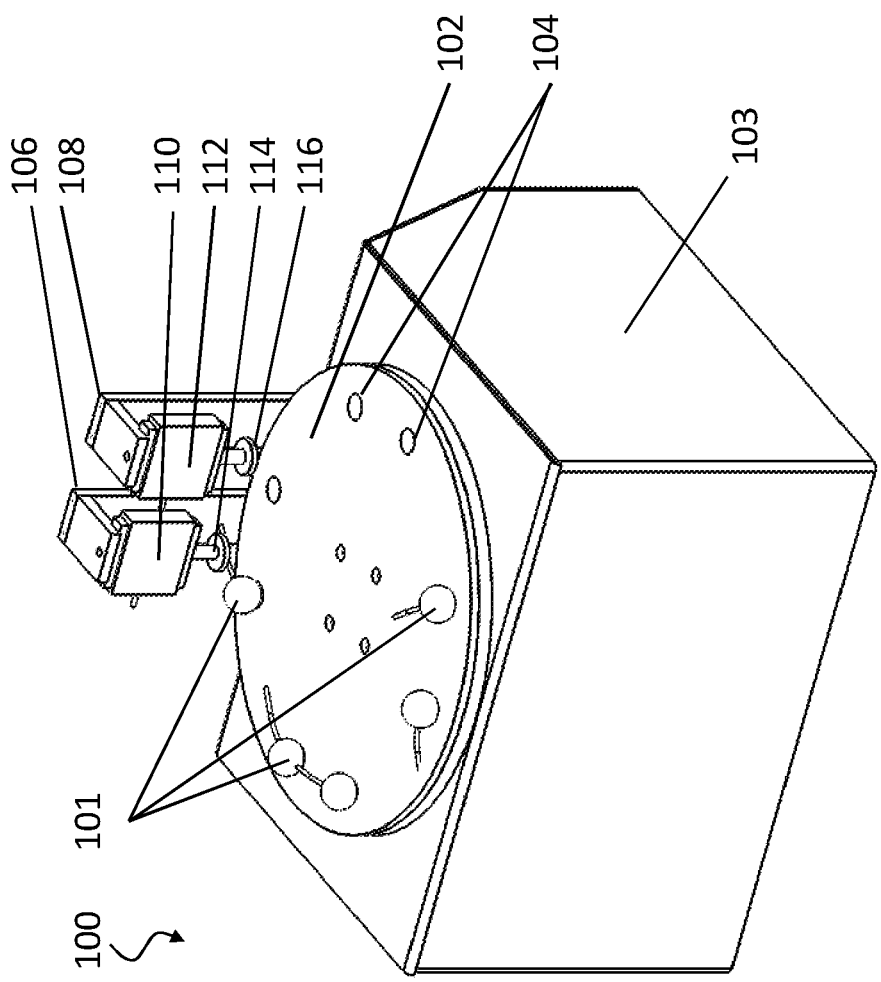
FIG. 1 shows an illustration of one embodiment of a fruit testing machine with twin sampling arms.

This application should be read in the most general possible form. This includes, without limitation, the following:

References to specific techniques include alternative and more general techniques, especially when discussing aspects of the invention, or how the invention might be made or used.

References to "preferred" techniques generally mean that the inventor contemplates using those techniques, and thinks they are best for the intended application. This does not exclude other techniques for the invention, and does not mean that those techniques are necessarily essential or would be preferred in all circumstances.

References to contemplated causes and effects for some implementations do not preclude other causes or effects that might occur in other implementations.

References to reasons for using techniques do not preclude other reasons or techniques, even if completely contrary, where circumstances would indicate that the stated reasons or techniques are not as applicable.

Furthermore, the invention is in no way limited to the specifics of any particular embodiments and examples disclosed herein. Many other variations are possible which remain within the content, scope and spirit of the invention, and these variations would become clear to those skilled in the art after perusal of this application.

Specific examples of components and arrangements are described below to simplify the present disclosure. These are, of course, merely examples and are not intended to be limiting. In addition, the present disclosure may repeat reference numerals and/or letters in the various examples. This repetition is for the purpose of simplicity and clarity and does not in itself dictate a relationship between the various embodiments and/or configurations discussed.

Read this application with the following terms and phrases in their most general form. The general meaning of each of these terms or phrases is illustrative, not in any way limiting.

References to a "Geneva" wheel generally apply to a mechanical device in the form of a disc, turntable, platen, wheel or similar rotatable device that has a plurality of grooves, indents, depressions or channels or similar cutouts that operate to engage with, guide or interact with a pin, dowel, rod, follower or similar mechanical linkage means that enables the Geneva wheel to be moved by means of engaging with the mechanical linkage means, or conversely enables the movement of the Geneva to be driven by means of the mechanical linkage. In practice, all variations and combinations of these mechanical disc-like devices, cutouts and mechanical linkages are suitable for use with embodiments of the instant invention.

Detailed Description

FIG. 1 shows an illustration of one embodiment of a fruit testing machine 100 with twin sampling arms that enable two objects or pieces of fruit to be tested simultaneously. In FIG. 1, a first sampling arm 106 is positioned adjacent to and above the turntable 102 and mechanisms not shown that are enclosed within the machine enclosure 103 to protect users from moving parts and electrical exposure. The first sampling arm 106 supports and terminates with a first fruit paddle 114 mounted to the first transducer unit 110. The first sampling arm 106 supports a first transducer unit 110 that operates to measure the applied force between the first fruit paddle 114, the fruit 101 (in this embodiment, cherries with stems) and the turntable 102 fruit well 104 in which the fruit being tested is positioned by the operator prior to testing.

In this embodiment shown in FIG. 1, an identical second sampling arm 106 is positioned adjacent to and above the turntable 102, and is positioned immediately adjacent to said first sampling arm 106 in a position that enables the second transducer unit 112 mounted on said second sampling arm 106 and also bearing a second fruit paddle 116, to simultaneously interact with and measure the applied force between the second fruit paddle 116, any fruit 101 present in the second well (shown unoccupied) and the turntable 102 fruit well 104 corresponding to the position of the second piece of fruit (not shown).

Accordingly, in this embodiment of the disclosure the fruit testing machine 100 may operate to simultaneously test two different pieces of fruit at the same time, by first indexing the turntable 102 rotationally (in either direction, clockwise or counter-clockwise) so that a first piece of fruit and a second piece of fruit are each independently located in their own respective fruit well 104 immediately adjacent to and below the corresponding first and second sampling arms 106 and 108, respectively. In this configuration, the fruit testing machine 100 can simultaneously measure the firmness or ripeness (essentially the compression characteristics thereof) of any two objects, measuring them simultaneously but independently using a first and second transducer unit 110 and 112 terminated with a first and second fruit paddle 114 and 116, respectively, which are lowered into contact with the fruit by means of the respective first and second sampling arms being lowered in height with respect to the top surface of the turntable 102.

In other embodiments of the disclosure, the fruit testing machine 100 may operate to sequentially test single pieces of fruit one at staggered times by employing either or both sampling arms and transducer units, and then indexing the turntable 102 rotationally in a direction and over a selected angle sufficient to bring at least one of said fruit wells into a position immediately underneath one or more of the sampling arms of the inventive device.

In further embodiments of the disclosure, the fruit testing machine may include just one, or a plurality of sampling arms and the respective transducer units and fruit paddles to enable the measurement of one (1), two (2) or more objects (3+) simultaneously.

In one embodiment of the disclosure, a test device or sample blank having known physical characteristics (such as compression force, elasticity, deformation coefficient, etc.) can be placed into one or more of the sampling (fruit) wells 104 and subjected to the same measurement test as a fruit 101 for the purposes of machine calibration and testing. In one non-limiting example, the test device is a piece of rubber or similar deformable elastic material that can be compressed and trusted to return to its initial pre-deformed state consistently without changing behavior over a selected number of cycles so as to serve as an independent and repeatable control for measuring compression forces and compression profiles, the latter being the histogram or plot of the resistant force over a period of time or as a function of applied force with respect to the test object and the distance movement or displacement of the fruit paddle/transducer from the initial point of contact with the test object (fruit) and the fruit paddle.

In another embodiment of the disclosure, the test device or sample blank can be positioned in a manner so that it is first tested by the first sampling arm 106 and corresponding first transducer unit 110, then repositioned by indexing the turntable 102 so that the fruit well 104 in which the test device was originally placed is next positioned in a manner to then be tested by the seconding sampling arm 108 and corresponding second transducer unit 112. This enables the first and second transducer units to be measured and calibrated, and compression data and characteristics of the test device saved for reference or comparison to the results and measurements of the desired object or fruit pieces to be tested by the inventive fruit testing machine 100.

In yet a further embodiment of the disclosure, the test device or sample blank can be positioned adjacent to one or more test objects or pieces of fruit 101 on the turntable 102 in adjacent fruit wells 104 so that the first and second sampling arms 106 and 108 can be used to simultaneously yet independently measure the compression characteristics of the test device and an adjacent piece of fruit to enable a side by side control measurement.

Figure 2:
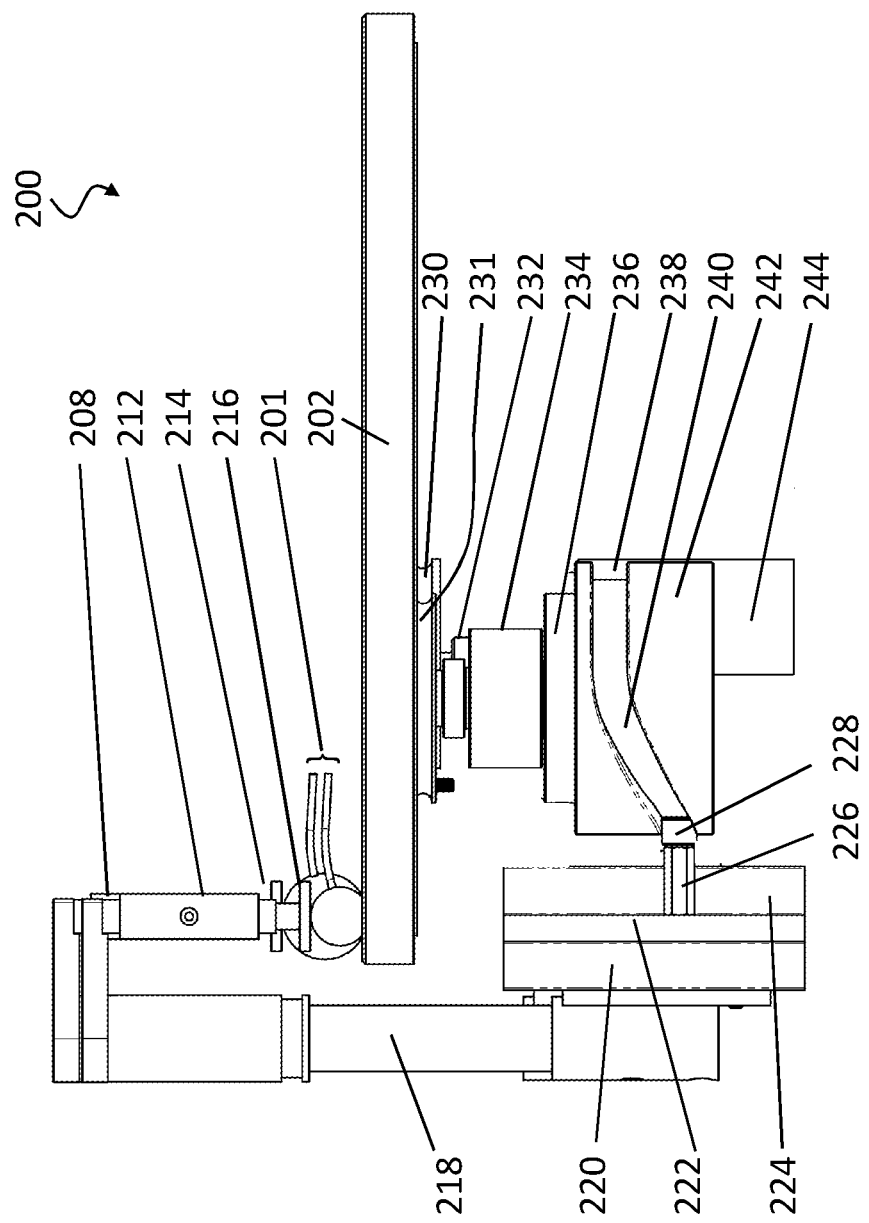
FIG. 2 shows a side view illustration of one embodiment of a fruit testing machine showing the sampling arms and fruit paddles in a position engaged with a fruit undergoing testing.

FIG. 2 shows a side view illustration of one embodiment of a fruit testing machine 200 showing the sampling arms and fruit paddles in a position engaged with two pieces of fruit 201 (cherries with stems) undergoing testing. Here, the side view shows only the first sampling arm 208 and first riser 218 that supports the sampling arm and which translates vertically (up and down) with respect to the upper flat surface of the turntable 202 that bears sampling (fruit) wells (as shown in FIG. 1) that hold the respective pieces of fruit 201 in position and in alignment (here, preferentially with stems pointing approximately radially towards the center point of the turntable 202.

Figure 10:
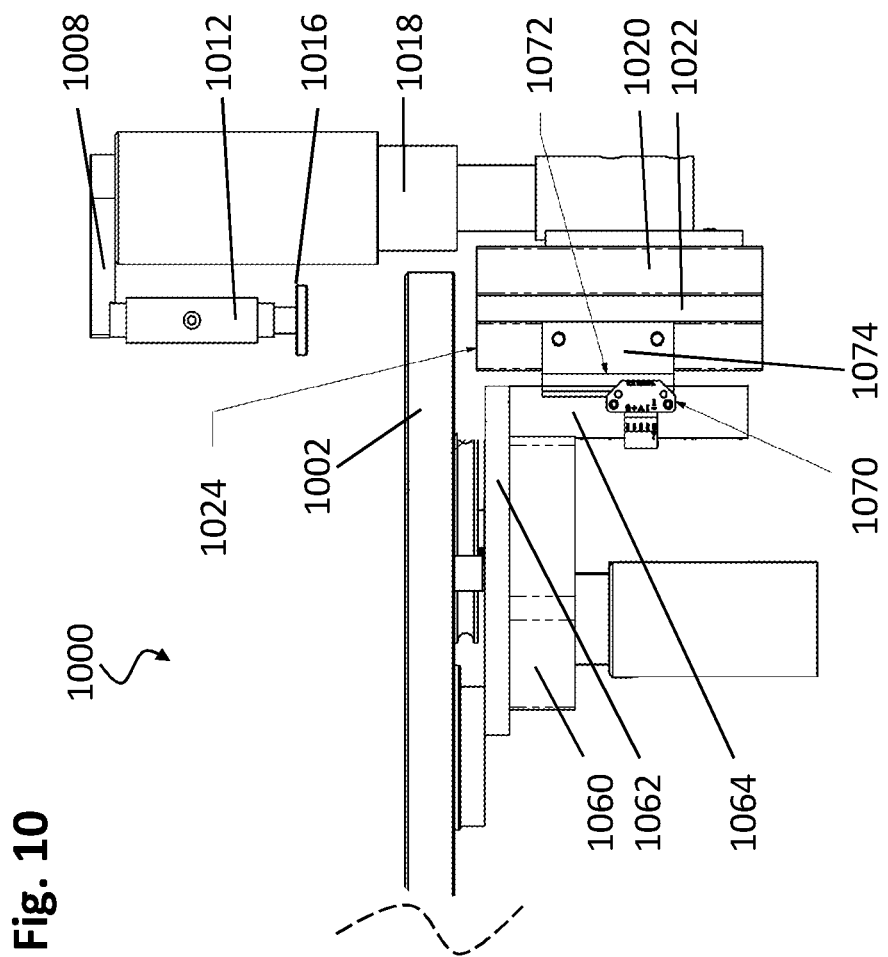
FIG. 10 shows a side view illustration of one embodiment of a fruit testing machine showing details of the encoder assembly and components associated with the second riser assembly.

FIG. 2 further shows one embodiment of the disclosure wherein a direct current (DC) motor 244 is used to rotate a three-dimensional (3D) cylindrical rotary cam 242 that has grooved cam surface 238 including a cam channel 240 in which a cam follower 228 attached to the terminal end of a cam follower shaft 226 is engaged in a manner that results in said came follower 228 to be vertically translated (up and down) from a low position to a high position (see FIG. 10 for additional detail). In said high position, the 3D cylindrical rotary cam 242 is oriented (rotated to a first or rest position) so that the cam channel 240 is at its highest position with respect to the cam follower 228, and in said low position the 3D cylindrical rotary cam 242 is oriented (rotated to a second or testing position) so that the cam channel 240 is at its lowest position with respect to the cam follower 228.

In one embodiment of the disclosure, FIG. 2 shows the cam follower shaft 226 which passes through (not shown) the riser encoder slide 224, which is in a fixed position and which engages with the cam follower plate 222 which in turn couples with the first unit slide 220 which supports the first riser 218 assembly. Accordingly, when the 3D cylindrical rotary cam 242 is in the position shown in FIG. 2, the cam follower 228 and cam follower shaft 226 are in the low position corresponding to the testing position of the first riser 218 and the second riser (not shown) in which the corresponding first fruit paddle 214 and second fruit paddle 216 have been lowered into a testing position with fruit 201 in their corresponding fruit wells and positioned for measurement by the corresponding first transducer unit 212 and the second transducer unit (not shown).

Also shown in one embodiment in FIG. 2 are components of the turntable 202 lower assembly, which provides the means to rotate the turntable 202 in a controlled and precise manner to advance it (optionally clockwise or counterclockwise) to the next test position, which may optionally be one, two, three or any desired integer, depending on whether the device is configured to take a single reading per cycle, or two or more readings per cycle, in embodiments featuring one or a plurality of sampling arms configured above the corresponding sampling (fruit) wells located on the upper surface of the turntable 202.

The turntable 202 lower assembly in this embodiment includes a gear motor pulley 230 that communicates with a gear box 232 enabling the rotation of the turntable 202, and a Geneva drive pulley 231 attached below and connecting with a drive bearing (not shown) protected by a drive bearing housing 234 which is attached to a lift cam mount flange 236 to which the 3D cylindrical rotary cam 242 is attached. A DC motor 244 is connected to the gear motor pulley 230 and operates to drive the gear box 232 which operates to turn the respective gear motor pulley 230 and the Geneva drive pulley 231 which maintaining the respective components in a fixed co-alignment so that the elements are aligned properly to advance the turntable 202 the desired degree of rotation while simultaneously driving the rotation of the 3D Cylindrical rotary cam, which communicates with the cam follower plate 222 by means of the cam follower 228 and cam follower shaft 226 to raise and lower the respective second (not shown) and first riser 218 that is attached to the movable cam follower plate 222 that is sandwiched between the riser encoder slide 224 and unit slide assemblies, in this embodiment as shown in FIG. 2 being the first unit slide 220.

Figure 4:
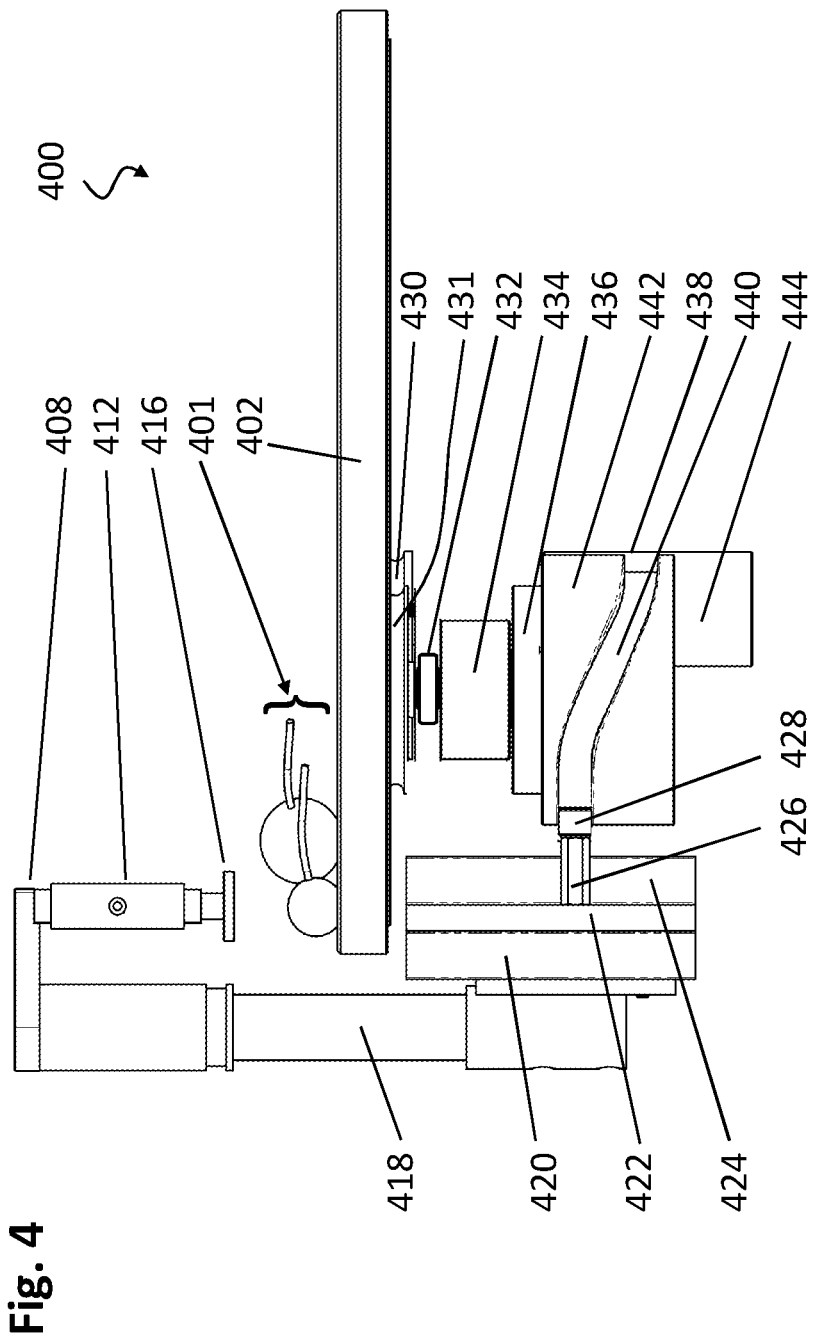
FIG. 4 shows a side view illustration of one embodiment of a fruit testing machine showing the motor mechanism and three dimensional (3D) cylindrical cam and cam follower assembly.

Here, the device is shown in FIG. 2 in a fruit sampling position, to be contrasted to the device in a fruit loading or non-testing position to be detailed further in discussion of FIG. 4.

Figure 3:
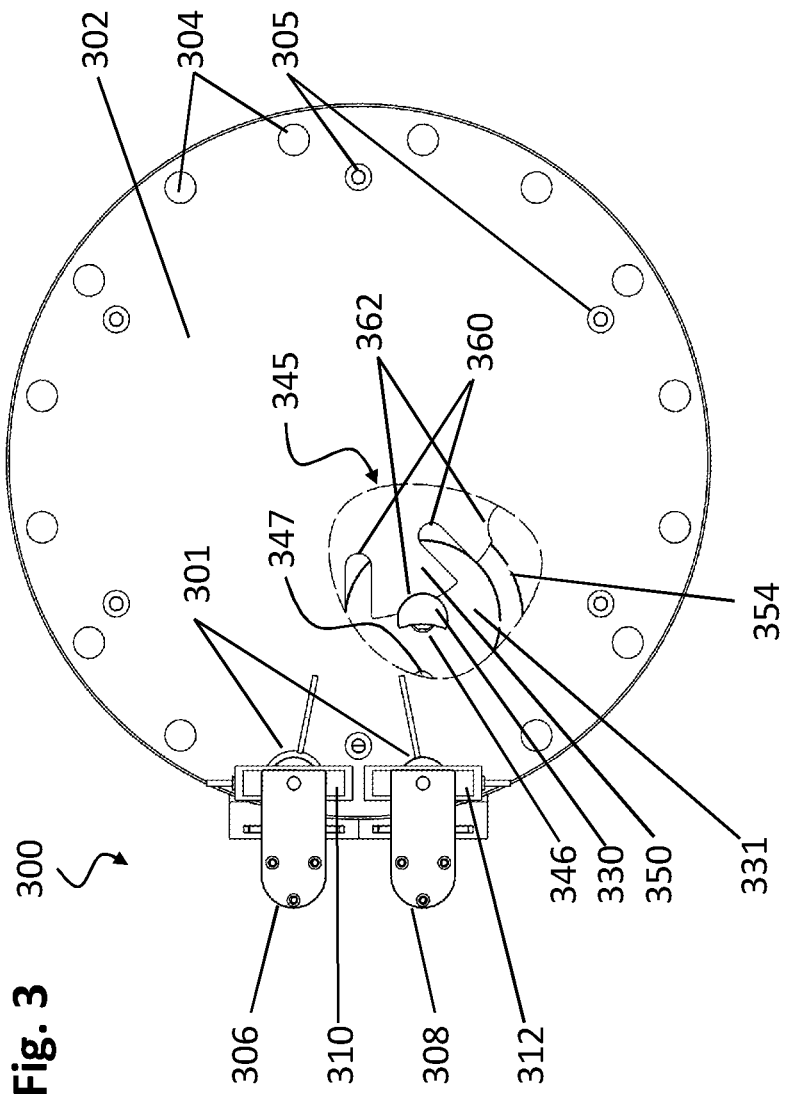
FIG. 3 shows a top view illustration of one embodiment of a fruit testing machine with a cutaway view of the Geneva drive pulley, Geneva turntable indexing wheel, keyed drive shaft and Geneva blocking disc mechanisms.

However, FIG. 3 shows a top down view of the inventive fruit testing machine 300 with a partial cut-away view indicated by the dashed region 345 in order to show that part of the drive assembly located under the device turntable 302 which provides the means to rotate the turntable 302 as desired.

In FIG. 3, the Geneva driving pin 347 located on the surface of the Geneva drive pulley 331 has previously positioned the Geneva turntable indexing wheel 350 into the desired position by having previously engaged with one of the Geneva drive indents 360 during the rotation of the Geneva drive pulley 331 and the pin 347 has now rotated out of contact (as shown in FIG. 3), enabling the Geneva blocking disc 330 to mate with one of a Geneva blocking stop indents 362 located on the perimeter of the Geneva turntable indexing wheel 350, which operates to secure the turntable 302 in a fixed and locked position during the test cycle. Also shown in this embodiment in FIG. 3 is the keyed drive shaft 346 which connects to the Geneva drive pulley 331 and operates to rotate the Geneva blocking disc 330.

In this embodiment of the fruit testing machine 300, the position of the Geneva drive pulley 331 also operates to rotationally position the three dimensional (3D) Cylindrical cam 354 into a position enabling it to interact with the cam follower (not shown) which drives the raising and lowering movements of the first and second sampling arms 308 and 306, respectively, which when lowered engage the respective test objects or fruit 301 located in the corresponding fruit wells 304 that are located immediately below the respective first and second sampling arms which operate to bring the corresponding first and second transducer units, 312 and 310, into contact with the fruits 301.

Also shown in this embodiment are the turntable mounting screws 305 that serve to attach the turntable 302 to a support platform (not shown) that couples to the turntable indexing wheel 350.

FIG. 4 shows a side view illustration of one embodiment of a fruit testing machine 400 showing the turntable drive assembly (components 430-444) located below the turntable 402 with 3D cylindrical cam 442 and cam follower assembly (426, 428), wherein the machine is in a loading or pre-test configuration with the second (not shown) and first sampling arm 408 in the highest raised position of travel corresponding to the position in which the 3D cylindrical rotary cam 442 has been rotated bringing the cam follower 428 to its highest position, which via communication by means of the cam follower shaft 426 which engages with the cam follower plate 422 to position it, unit slide 420, riser encoder slide 424 and first riser assembly 418 at their highest point of travel, providing sufficient clearance between the raised sampling arm 408, the raised transducer unit 412 and the raised fruit paddle 416 to enable the loading and unloading of fruit 401 into respective fruit wells (not shown) located on the upper surface of the turntable 402 immediately below the respective positions of the second (not shown) and first sampling arm 408 and its respective components.

In operation, the embodiment of the fruit testing machine 400 shown in FIG. 4 enables the placement of one or a plurality of test objects or fruit 401 into corresponding sampling well located on the upper surface of the turntable 402. An operator would position the fruit so that any stems would point inwardly toward the center of the turntable 402 in order to prevent the stems from touching or getting caught by other components of the machine. At this stage, one or more of the wells can be loaded with fruit, and then the turntable 402 rotated one step (optionally clockwise or counter-clockwise) into either a first measurement position for the purposes of conducting a calibration measurement using a test object or for the purpose of a testing a first piece of fruit, wherein said one step results in the movement of the turntable 402 sufficient to bring the fruit piece 401 in its respective sampling well (not shown) into position immediately below the first sampling arm 408.

Alternatively, in another embodiment, the turntable 402 can be rotated two steps, again optionally clockwise or counter-clockwise) into a first and second measurement position wherein the two steps results in the movement of the turntable 402 sufficient to bring a first fruit piece and a second fruit piece (401) in their respective sampling wells into positions immediately below the respective first sampling arm 408 and the second sampling arm (not shown).

In the embodiment of the disclosure shown in FIG. 4, the Geneva drive pulley 431 has been positioned by means of the DC motor 444 and gear motor pulley 430 communicating a rotational movement by means of the driving bearing 432; said position placing the respective fruit pieces 401 into the proper position for subsequent testing, the testing configuration corresponding to the embodiment of the device and relative position of the components as shown and discussed with regard to the preceding FIGS. 2 and 3.

Figure 5:
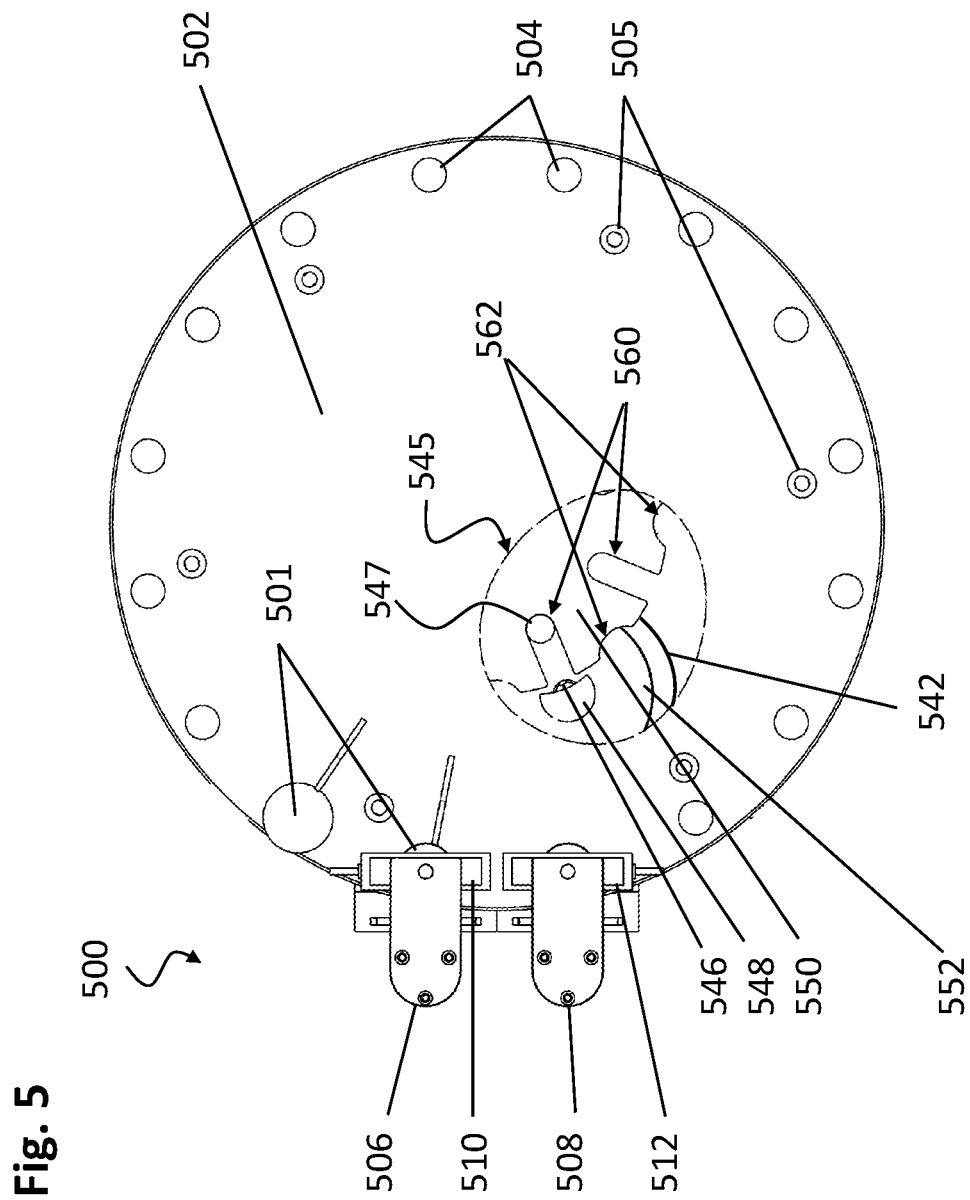
FIG. 5 shows a top view illustration of one embodiment of a fruit testing machine with a cutaway view of the Geneva drive pulley, Geneva turntable indexing wheel, keyed drive shaft and Geneva blocking disc mechanisms rotated to engage the Geneva driving pin and position the fruit to be tested.

FIG. 5 shows a top view illustration of one embodiment of a fruit testing machine 500 in a configuration matching that of the embodiment shown in FIG. 4. FIG. 5 shows a cutaway view of the Geneva turntable indexing wheel 550 and keyed drive shaft 546 rotated to engage the Geneva driving pin 547 with the Geneva turntable indexing wheel 550 and disengage the Geneva blocking disc 548 so as to raise the first and second sampling arms (508 and 506) to their highest position with respect to the upper surface of the turntable 502 to enable sufficient clearance for the loading and/or removal of test objects or fruit from the respective fruit wells 504.

In the embodiment shown in FIG. 5, the Geneva turntable indexing wheel 550 has been rotated into its indicated position as shown by means of the keyed drive shaft 546, thereby operating to position the Geneva drive pulley 552 that bears a Geneva driving pin 547 on its upper surface and which subsequently engages with at least one of the Geneva drive indents 560 which operates to lock the turntable 502 in position and prevent rotation or motion during the test object or fruit loading or unloading from the turntable fruit wells 504. In this embodiment, the rotational position of the keyed drive shaft 546 operates to position the Geneva blocking disc 548 into a clear or unengaged position from one or more of the Geneva blocking stop indents 662, the shallow indents located on the outer perimeter of the Geneva blocking disc.

In the embodiment in FIG. 5, the Geneva turntable indexing wheel 550 is attached to the bottom surface of the turntable 502 and co-aligned with the center rotation of axis of the turntable 502, so that it operates to turn or 'index' the turntable from a first position to a second desired position for the process of loading and unloading test objects/fruit pieces and for the purpose of taking repeated and sequential measurements of test objects located in fruit (sample) wells on the turntable surface.

In additional embodiments, the number and positioning of the Geneva drive indents 560 and the Geneva blocking stop indents 562 located on or adjacent to and contiguous with the outer perimeter of the Geneva turntable indexing wheel 550 are selected to match the number of the fruit wells 504 located on the upper surface of the turntable 502, and the positioning, or rather the relative positioning between adjacent Geneva blocking stop indents 562 and/or adjacent Geneva drive indents 560 corresponding to the same angular separation as that between two adjacent fruit wells. By way of example, the embodiment as shown in FIG. 5 has sixteen (16) fruit wells 504 that are radial or equidistantly spaced along a circumferential (rotational) axis that is proportional to the circumference of the turntable 502, and thus being rotational separated by 360°/16 or 22.5° (degrees). In other embodiments of the instant disclosure, the turntable 502 can feature any integer number of sample or fruit wells 504 from 2 to about 50, the number selected being dependent on the number of desired samples or fruit pieces 501 to be placed on the turntable 502 for testing, multiple turntable mounting screws 505 securing the turntable 502 to a Geneva drive wheel 550 driven by the 3D cylindrical rotary cam 542.

The number of fruit wells 504 depends to some extent on the size of the test object or fruit 501 being tested. Larger fruit like apples, pears, peaches, avocados and the like, require larger fruit wells 504 and thus fewer can be accommodated on a particular sized turntable. Smaller fruit like grapes, cherries, cherry tomatoes, olives and the like, require smaller fruit wells 504 and thus more fruit wells can be accommodated on the same particular sized turntable than with the larger fruit. In related embodiments, the turntable 502 can be of any desired size, limited only by the desired size of the machine and the size and number of test objects or fruit pieces desired to be loaded onto the turntable for subsequent testing. In further embodiments of the disclosure, the turntable 502 can have two or more sets of differently sized fruit wells, for example a plurality of large and small fruit wells that are interleaved (alternating) with respect to one another, having the same relative radial spacing with respect to the adjacent similar fruit well, or in other words, both sets of wells are equally spaced about the circumference, so that the operator would have the choice of loading either a smaller set of large fruit into their corresponding and necessarily smaller number of large fruit wells, or a larger set of smaller fruit into their corresponding and necessarily larger number of small fruit wells, without having to change the turntable to measure different fruit or fruit of different sizes.

In some embodiments, the number of fruit wells is selected to be an odd integer, i.e. 3, 5, 7, etc. In other embodiments, the number of fruit wells is selected to be an even integer, i.e. 2, 4, 6, 8, 10, etc. In these two prior embodiments, the degree of angular separation would be determined by simply dividing the total number of desired fruit wells into 360°, representing the full angular rotation or circumferential angle, with each well angularly spaced by an equal angle with respect to each other.

In these and related embodiments, the design of the Geneva turntable indexing wheel is selected so that the number and position of the Geneva drive indents and Geneva blocking stop indents corresponds to the number and position of the fruit wells, so that the drive mechanism of the fruit testing machine operates to position the fruit wells in proper alignment with the one or more of the sampling arms by means of the Geneva turntable indexing wheel's indents operating to assist in the positioning and locking of the turntable as well as the unlocking and rotational advancement of the turntable to the next testing position.

In these and relate embodiments, the design of the 3D cylindrical rotary cam is selected so that it operates to raise and lower the one or plurality of sampling arms an integer number of times per full rotation of the 3D cylindrical rotary cam. In some embodiments, the 3D cylindrical rotary cam features a cam channel on the grooved cam surface wherein the cam channel spans over a 360° rotation from a high position to a low position and back to the high position on the surface of the 3D Cylindrical cam, or in other words, operates to drive the associated cam follower engaged with the cam channel from a high position to a low position twice per full rotation of the 3D cylindrical rotary cam about its axis, resulting in the cam follower being repositioned to the same relative starting point (at which stage of rotation of the 3D cylindrical cam) after a full, 360° rotation of the rotary cam. In other related embodiments, the cam channel design can be selected so as to enable the cam channel to span across an integer number of high to low position per rotation. For visualization purposes, in one embodiment of the disclosure, the cam channel essentially corresponds to a sinusoidal channel form into the surface of the 3D cylindrical cam with a periodicity of 1 in order to raise the cam follower once per rotation, corresponding to the crest of the sine wave that corresponds to the relative height of the cam follower with respect to the angular rotation of the 3D cylindrical cam about its axis. In a closely related embodiment, the cam channel can be formed to correspond to a sinusoidal channel with a periodicity of two (2) in order to raise the cam follower twice per rotation, corresponding to the two subsequent crests of the sine wave, which would then correspond to two subsequent high positions on the grooved cam surface. In both of the previous embodiments, the trough or bottom of the sine wave corresponds to the low position on the grooved cam surface, which operates to lower the cam follower to the low position when this portion of the sinusoidal cam channel is engaged with the cam follower during the rotation of the 3D cylindrical cam.

In other embodiments of the disclosure, the number of sampling stations (arms and assembly) can be selected from an integer number from 1, 2, 3, 4 and so forth, determined in part by the desired number of simultaneous measurements of test objects of fruit pieces to be made, and limited only by practical considerations relating to the size of the resulting turntable and corresponding complexity of the instrumentation. The selection of the number of sampling stations determines the number of simultaneous measurements that can be made per one cycle of the fruit testing machine of the disclosure. In embodiments with one sampling station, a single measurement (or repeated measurement at the same station) can be completed per cycle, or one index of the turntable to position the next sample to be tested at the position of the single sampling station. In embodiments with two sampling stations, two simultaneous measurements of a first and second sample can be made per cycle, or without moving the turntable during the test cycle, by rotating the turntable so that a first fruit in a first fruit well is positioned under the first sampling station while an adjacent second fruit in an adjacent second fruit well is positioned under the second adjacent sampling station, and both are measured at the same time by the first and second sampling arm and corresponding transducer, respectively.

An alternative embodiment of the present disclosure featuring two sampling stations is possible wherein the first test object or fruit piece located in a first well on the turntable is position under the first sampling station which is activated to take a measurement during one cycle, then the turntable is rotated in a manner to bring that first test object or fruit piece under the second sampling station, which is then activated to take a second measurement during a subsequent second cycle.

In yet another alternative embodiment, a test object or calibration device, such as a rubber ball or spring cylinder with know and reproducible compression properties may be substituted for a first or second test object or fruit piece in two adjacent fruit wells in order to provide a calibration test result on the test object under identical circumstances as subjected by fruit undergoing testing. In related embodiments, the test object or calibration device can be tested singly, or tested simultaneously with one or a plurality of actual fruit pieces to provide a simultaneous calibration curve and actual test measurement. In yet another embodiment, the test object or calibration device can first be measured in the first test station, followed by a rotation of the turntable to bring it into position at a second test station whereat a second measurement can be made, allowing the measurements or output of the first and second test station (the first and second transducer unit) to be compared and/or calibrated as desired.

Figure 6:
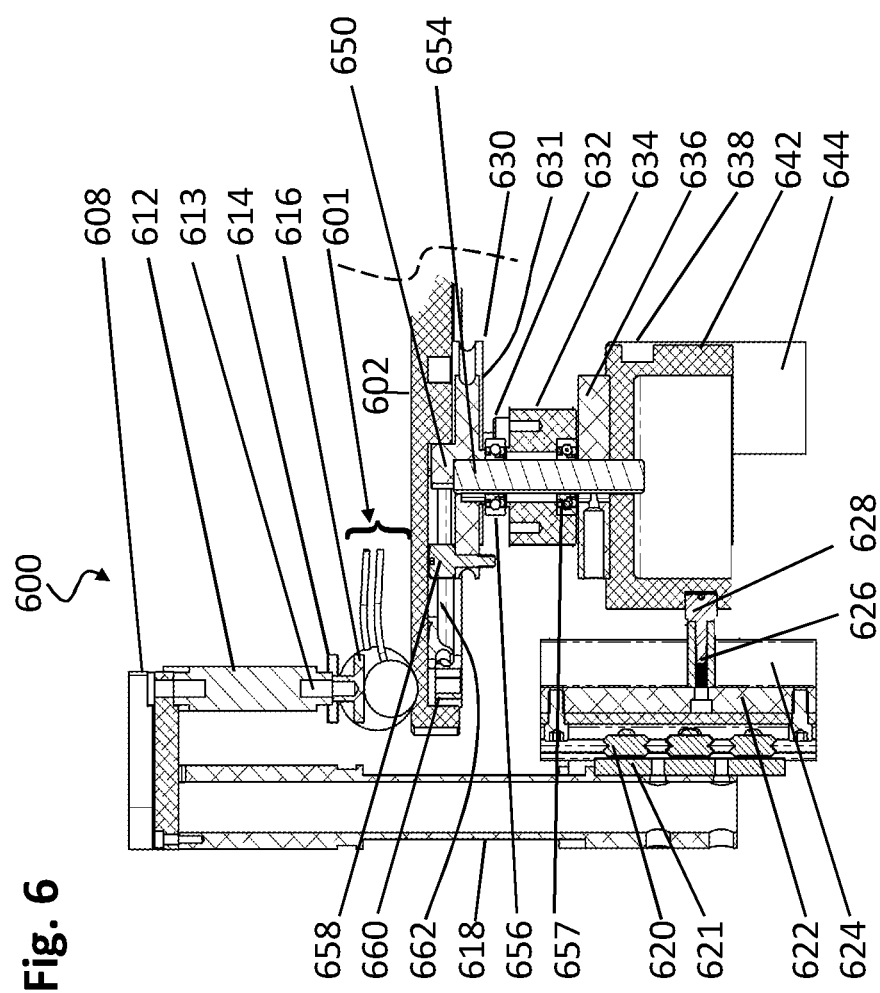
FIG. 6 shows a side view cutaway illustration of one embodiment of a fruit testing machine showing inner details of the motor mechanism, riser assemblies, turntable, Geneva gear and 3D cylindrical cam and cam follower assembly.

FIG. 6 shows a side view cutaway illustration of one embodiment of a fruit testing machine showing cross-cut details of the drive means, riser assemblies, turntable, Geneva gear and 3D cylindrical cam and cam follower assembly.

In one embodiment, the sampling arm 608 (first) is fixedly supported and attached to a riser tube 618 (first riser) by any suitable means, an example being the use of a cap plate (not labelled) that attaches to the riser tube and the sampling arm, and which holds them in fixed relative position and of sufficient strength and rigidity to bear the weight of the assembly. In another embodiment, the riser tube 618 is fixedly attached to first slide carriage coupling plate 621 which is held in place by a guide (not shown) that engages one or more of a slide vee ("V") roller 620 so that the carriage coupling plate is vertically movable from a (low) start position to a (high) stop position, aided by the slide vee roller 620 to maintain a fixed horizontal orientation during the vertical translation of the riser, basically enabling the riser to only go up or down without any significant sideways or other out of normal (vertical axis with respect to the planar surface of the turntable 602) deviation during its travel between a low and high position. Although a first riser 618 configured in the form of a hollow tubular structure is exampled, any suitable mechanical means to fixedly support the sampling arm and transducer unit and couple the sampling arm to one of the slide carriage plates is acceptable, although it is desirable to reduce the weight of the assembly for practical considerations. In general embodiments of the invention, each riser assembly includes the riser component, a sampling arm, a sensor element such as but not limited to a transducer, and other components of assembly including screws, nuts, washers, braces, brackets and other attachment means for assembling the components of the riser assembly as shown and described in the related embodiments as disclosed.

In FIG. 6, the cutaway view shows additional details of how the Geneva drive pulley 631 engages with the Geneva driving pin 658 on the top engagement surface of the Geneva drive pulley 650 which is rotationally driven by the gear motor pulley 630 by means of a drive belt (not shown) that couples the Geneva drive pulley 650 and the gear motor pulley 630. In related embodiments, the means of rotationally driving the Geneva assembly may further include, and is not limited to, a drive belt, drive chain, ball chain, and the like. In yet another related embodiment, the means of rotationally driving the Geneva assembly may include the use of gears instead of a pulley system to couple the Geneva assembly to the gear motor. In this embodiment shown, the Geneva driving pin 658 engages with the Geneva drive indents (not shown) located on the outer or peripheral surface or engagement surface of the Geneva turntable indexing wheel (not detailed) that couples to the bottom surface of the turntable 602.

In FIG. 6, the cutaway view shows one means of coupling the keyed drive shaft 654 to the Geneva drive pulley 631 which drives the turntable 602 rotationally about the axis of the keyed drive shaft 654, the turntable 602 supported by a ball bearing outer race 660, optionally attached to said turntable, and which enables free rotation of the turntable 602 in conjunction with a ball bearing inner race 662, optionally attached to the machine closure (not shown), or other support means that operates to hold the inner race 662 in co-alignment with the ball bearing outer race 660 and enable the rotation of the turntable 602 by means of the relative movement of the Geneva drive pulley 631 about the keyed drive shaft 654 axis.

Also shown in one embodiment in FIG. 6, are a set of an upper drive shaft bearings 656 and lower drive shaft bearings 657 that support the center keyed drive shaft 654 and which operate to enable the drive shaft to freely rotate about its axis while maintaining it in position and vertically aligned with respect to the plane of turntable 602 (i.e. perpendicular) and the 3D cylindrical rotary cam 642. In this embodiment, the keyed drive shaft 654 is coupled to the Geneva drive pulley 631 by means of a key fitment between the drive shaft and the drive pulley mechanisms. Also shown in FIG. 6 is the drive bearing housing 634 that supports the set of upper and lower drive shaft bearings 656 and 657, respectively, holding them in fixed position to enable the rotation of the center keyed drive shaft 654 which passes through the sets of drive shaft bearings as disclosed.

In the embodiment shown in FIG. 6, the center keyed drive shaft 654 passes through the lift cam mounting flange 636 to mechanically couple with the 3D Cylindrical cam 642, which then accordingly operates to rotate with the drive shaft, rotating about an axis coincident and axially aligned with that of the drive shaft. As the 3D Cylindrical cam 642 rotates, its surface rotates with the grooved cam surface 638 thus operating to engage the cam follower 628 and cause it to move in a perpendicular or up and down direction with respect to the rotational axis of the 3D cylindrical cam 642, as the cam follower 628 engages with and moves along the rotationally changing aspect of the grooved cam surface 638 which acts as a channel to guide the cam follower, which is held in the groove of the cam by means of the cam follower shaft 626 which couples the cam follower with the cam follower plate 622, which in turns moves perpendicularly or up and down with respect the rotational axis of the 3D cylindrical cam 642. In some embodiments of the disclosure, the cam follower plate 622 operates as a mount or support for one or a plurality of riser slide mounts, providing a common anchor point for the measuring arm's linear slides, for example, the first riser encoder slide 624 as shown in FIG. 6.

Also shown in FIG. 6, is one embodiment of the drive mechanism for the inventive device that employs a DC motor 644 that is coupled to a gear box 632 that operates to either increase or reduce the output speed of the motor (revolutions per minute or rpm) with internal gearing to within a desirable rotational speed or rpm, or alternatively to within a range of speeds and rpms, in order to drive the mechanism of the inventive device. In related embodiments, other drive mechanisms may be employed as a drive mechanism, including, but not limited to mechanical devices such as cranks, hand cranks, clockworks, spring works, pistons, compressed air and fluidic systems, hydraulic systems, and ratcheting levers, cams, and gearing, and the like as well as other mechanical means of providing rotational force with sufficient torque to operate the inventive device. In further embodiments, other drive mechanisms may be employed, including, but not limited to electrical devices such as AC motors, asynchronous motors, synchronous motors, DC motors, DC gear motors, stepper motors, linear and rotational actuators, and the like as well as other electrical and electromechanical means of providing rotational force with sufficient torque to operate the inventive device.

In the embodiment shown in FIG. 6, the DC motor 644 is connected to and operates to drive the gear box 632, which is connected to and operates to drive the gear motor pulley 630. The gear motor pulley 630 operates to drive the Geneva drive pulley 631 by means of a drive belt (not shown). In other embodiments, other means to drive the Geneva drive mechanism are possible, including the use of gears, gear boxes, mechanical couplers, chains, ball chains, drive chains and the like that are capable of transmitting mechanical motion and torque to the Geneva drive mechanism to affect its (rotational) movement in either a clockwise or counterclockwise direction.

As illustrated in FIG. 6, in embodiments in which there are two or more sampling assemblies, a first transducer element 613 attached to a first transducer unit 612 and its fruit paddle 616 and a second transducer element (not shown) and a second fruit paddle 614, operate to engage the test object or fruit independently of each other, in other words the first and second sampling arms move independently of one another in order to accommodate different sized test objects of fruit pieces 601 that are placed in the fruit wells corresponding to the positions of the first and second sampling arms.

In related embodiments featuring three or more sampling assemblies, each of the assemblies (which includes a sampling arm, a transducer unit, a fruit or object paddle, a riser, and a unit slide and other components thereof) all operate independently of each other with respect to their being vertically positionable by means of their own carriage coupling plate, which are driven upwards and downwards by means of the cam follower shaft that couples to the cam follower plate. In related embodiments, the one or plurality of sampling assemblies are all driven upward simultaneously by means of the common carriage plate that is driven by the cam follower shaft moving along the cam follower groove by means of the cam follower achieving a high position with respect to the 3D cylindrical cam, yet however all sampling assemblies can move independently of each other on the downstroke of the common carriage plate owing to the sampling assemblies each coupling to the common carriage plate by means of their own carriage coupling plates that ride within their own respective slide carriage supported by one or more slide vee rollers.

Figure 7:
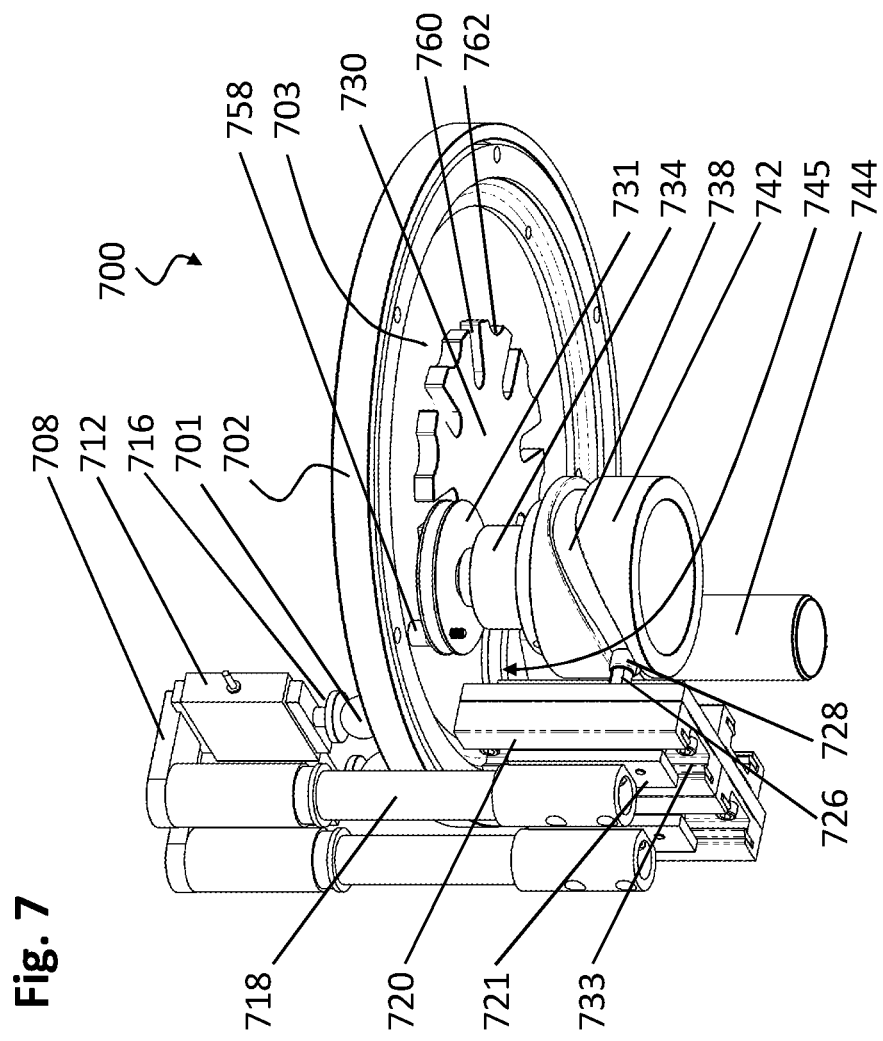
FIG. 7 shows an angled bottom view illustration of one embodiment of a fruit testing machine showing the motor mechanism and 3D cylindrical cam and cam follower assembly associated with the Geneva gear.
Figure 8:
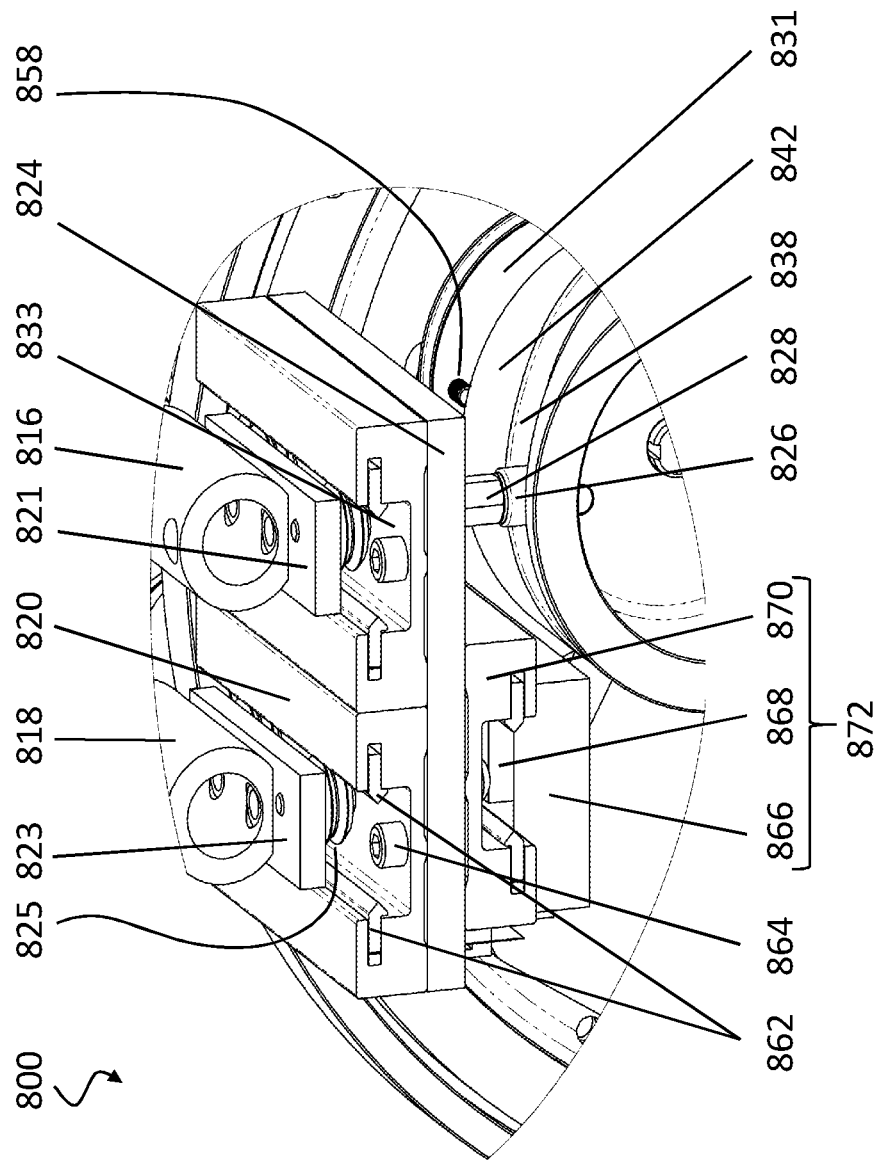
FIG. 8 shows an angled bottom view illustration of one embodiment of a fruit testing machine showing the first and second riser assembly mechanism and components and 3D cylindrical cam and cam follower assembly engaged with the first and second slide units.

Additional details as to the movement of the Geneva drive mechanisms and components are shown in FIG. 7 and FIG. 8.

FIG. 7 shows an angled bottom view illustration of one embodiment of a fruit testing machine showing the motor mechanism, a DC motor 744 and 3D cylindrical rotary cam 742 with a grooved cam surface 738 engaging a cam follower assembly comprising a cam follower 728 and cam follower shaft 726 that engages with a cam follower plate (not detailed) which in turn couples to one or a plurality of slide carriage coupling plates, the first slide carriage coupling plate 721 being shown, which travels up and down with respect to the first unit slide track assembly, which consists of a first unit slide inner track 733 and associated sets of one or more bearings (not detailed) that enable the vertical movement of the unit slide assemblies within their own slide tracks.

Also seen in the embodiment of the disclosure illustrated in FIG. 7 is the Geneva turntable indexing wheel 730 which is attached to the bottom side or turntable base 760 of the turntable 702. In this illustration, the Geneva drive pin 758 is seen coupled with the Geneva drive pulley 731 in a position in which the drive pin is rotated into contact with one of the plurality of Geneva blocking stop indents 762 located on the peripheral or outer surface of the Geneva turntable indexing wheel 730. In this embodiment, the position of the Geneva turntable indexing wheel 730 in a blocked condition with engagement of at least one of the plurality of Geneva blocking stop indents 762 engaged with the Geneva drive pin 758 corresponds to the lowest or bottom position of the cam follower 728 and the first unit slide assembly attached to the cam follower plate (not detailed) attached to the first unit plate 720 and first unit slide 721 to which the first riser 718 is attached supporting the first sampling arm 708 having a first transducer unit 712 bearing a first fruit paddle 716 that is brought into contact with fruit 701 when the cam follower 728 is at the lowest or bottom position as shown.

FIG. 8 shows an angled bottom view illustration of one embodiment of a fruit testing machine 800 showing the first riser 818 and second riser 816 and their associated mechanism and components and 3D cylindrical cam 842 and cam follower assembly (cam follower 828 and cam follower shaft 826) coupled to the riser encoder slide 824. In one embodiment, the riser encoder slide 824 supports a first and second slide carriage plate 821 and 823, respectively, which in turn support a first and second riser 816 and 818, and which operates to move the risers up and down along a first unit slide groove 833 and a second unit slide groove (not labelled), enabled by a plurality of slide vee rollers 825 (the bottom most one shown) that engage with and are guided by a plurality of slide vee guides 862 that are located opposite one another on the two facing internal surfaces of the unit slide units so as to couple with the slide vee rollers 825 and enable smooth vertical movement of the riser assembly, the slide vee rollers 825 operating to freely rotate like bearings to prevent unnecessary friction between the riser assemblies and the unit slide assemblies. In further embodiments, each riser assembly can have a multiple number of slide vee rollers, such as for example two, one located approximately adjacent to the top and bottom of the respective slide carriage plates.

In related embodiments of the current disclosure, each riser assembly can have three or a plurality of slide vee rollers, configured in a manner in which at least one of the plurality of rollers is located proximate to the bottommost end of the unit slide and at least a second of the plurality of rollers is located proximate to the uppermost end of that unit slide, and additional rollers are placed approximately equidistantly between in order to enable a smooth movement of the carriage plates along the length of the unit slide. In additional embodiments, alternative means of enabling the one or plurality of riser assemblies to move vertically upwards and downwards in a smooth and uniform manner with reduced friction may be employed instead of vee rollers and slide vee guides, including for example, but not limited to, linear race, linear ball bearings, tongue-and-groove, pulley and cable systems and the like, which are capable of guiding the one or plurality of risers from an initial low position to an intermediate high position and back to the initial low position without significant motion out of the desired axis or plane of travel.

In related embodiments, the lowermost position of the corresponding first and second risers and their corresponding first and second slide carriage plates is determined by the lowest position achievable by the cam follower 828 and cam follower shaft 826 that operate to raise and lower the first and second slide carriage plate 821 and 823 as the 3D cylindrical rotary cam 842 rotates and the cam follower 828 rides within the groove on the surface of 842, the grooved cam surface 838 as indicated. Further, in one embodiment, the bottom travel of the respective risers can be limited by including a slide mount limit screw 864 that is positioned near the bottom of the respective unit slide groove and which operates to block the movement by physically constraining any further downward movement beyond a point at which the slide carriage plate 823 touches the slide mount limit screw 864. Also illustrated in FIG. 8 is the Geneva driving pin 858 portion showing the threaded engagement portion of the driving pin that threads into the top surface of the Geneva drive pulley and optionally extends further through the bottom of the Geneva drive pulley (not numbered).

In related embodiments, additional risers and their associated components can be added to the machine by placing an additional riser assembly on the riser encoder slide 824 assembly, coupled so that the additional risers move up and down in a similar manner as those disclosed in the current embodiments for the first and second risers 816 and 818.

In the embodiment shown in FIG. 8, the fruit testing machine 800 also features an encoder slide assembly 872 which consists of an encoder mount block 866 which travels within the encoder slide base 870 which features a plurality of slide vee guides (not labelled) that engage a carriage plate 868 that operate in a similar manner as the slide vee guides 862 associated with the second riser 818 embodiment described herein. The encoder slide assembly 872 may in one embodiment move upwards and downwards along its own riser assembly in a manner similar to the first and second riser assemblies as described herein. The encoder slide assembly 872 operates to provide a stable and reproducible distance of travel measurement in conjunction with an electrical position encoder unit (not shown here) which is capable of responding to and measuring a relative position of the encoder slide assembly 872 and may operate to reporting that position in the form of an electrical signal decodable as a relative position measurement unit communicated to the user in a form of, but not limited to, a current, a voltage or an analog or digital signal, or the like, or combination thereof, as desired. See FIG. 10 for additional disclosure relating embodiments of the encoder slide assembly 872.

Figure 9:
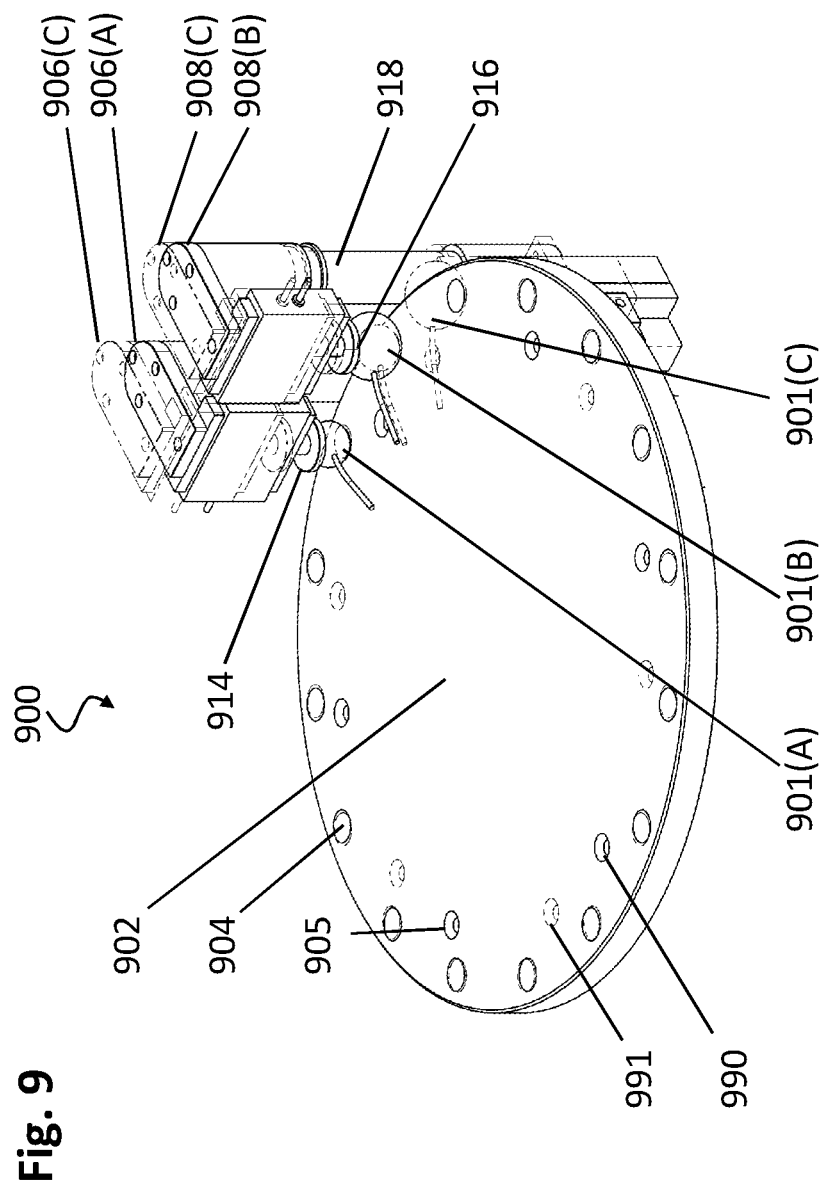
FIG. 9 shows an illustration of one embodiment of a fruit testing machine with two pieces of fruit positioned in testing mode following a single incremental rotation of the platform to advance a piece of fruit into a test position from an initial loading position.

FIG. 9 shows an illustration of one embodiment of a fruit testing machine 900 with two pieces of fruit 901 positioned in testing mode following a single incremental rotation of the platform to advance two pieces of fruit into test positions A and B from an initial loading position C.

In FIG. 9, the dotted components are used to illustrate a prior position of the component compared to that same component rendered in a solid line, the fruit testing machine 900 first being in a loading position C wherein the first and second sampling arms 906 and 908 are positioned in an initial raised configuration corresponding to said position C as indicated by 906(C) and 908(C), respectively. In this initial position C, the fruit wells 904 corresponding to a first small cherry or fruit piece 901(A) is positioned at a first well 904 of the turntable 902 and a second, large cherry or fruit piece 901(B) is positioned at a second well 904 that is immediately adjacent to said first well 904, there being one rotational stepwise movement of the turntable 902 required to reposition said second well to occupy the prior position of said first well, following either a clockwise or counter-clockwise rotation of the turntable 902 to advance a test object or fruit piece 901 into a position for measurement under one or more of a plurality of sampling arms.

Accordingly, in one embodiment, after at least a first and a second test object or fruit piece 901 is positioned on a corresponding series of adjacent fruit wells 904 on the turntable 902, the turntable may be indexed from the initial loading position C to a first measurement position B, in which the small cherry becomes positioned at the first test position immediately below the second sampling arm 908 (denoted so in order to be consistent with prior illustrations). A measurement cycle of the fruit testing machine 900 may be conducted at this point using the second sampling arm 908 with its corresponding fruit paddle 916 and transducer unit (not indicated) to conduct a test measurement cycle of said first fruit (small cherry) piece.

Alternatively, in a related embodiment, the measurement cycle of the fruit testing machine 900 may then be indexed to a second measurement cycle by means of indexing the turntable 902 to its next measurement position, which involves a single indexing of the turntable to move the first fruit piece (the small cherry) to a second test position immediately below the first sampling arm 906, while the second fruit piece (the large cherry) is repositioned to the first test position immediately below the second sampling arm 908. A measurement cycle of the fruit testing machine 900 may be conducted at this point using the second sampling arm 908 with its corresponding second fruit paddle 916 and transducer unit (not indicated) to conduct a test measurement of the second fruit (large cherry) piece simultaneously while using the first sampling arm 906 with its corresponding first fruit paddle 914 and transducer unit (not indicated) to conduct a test measurement of the first fruit (small cherry).

Alternatively, in further embodiments, one or more of the test objects 901 may include a standard test measurement device for the purposes of calibration and cross-calibration of the one or plurality of sampling stations and their corresponding sensor elements, such as for example the transducer units as described herein.

Additionally, FIG. 9 shows the relative position of the turntable 902 at the various positions A, B and C corresponding to a loading position and either a single or dual simultaneous measurement position, showing the advancement of the fruit wells in a (arbitrary) counter-clockwise movement as the turntable 902 turns counter-clockwise about its axis from a first turntable position 990 to a second turntable position 991, corresponding to positions A and B described above.

In related embodiments, the turntable of the inventive device may be positioned as needed, advanced to a position in which one or a plurality of test objects or fruit pieces are located beneath one or a plurality of sampling arms in order to be in a test position and capable of being measured using the corresponding sampling arm and its associated paddle and sensor element.

FIG. 10 shows a side view illustration of one embodiment of a fruit testing machine 1000 showing details of the encoder assembly comprising a riser encoder slide 1024, a riser encoder mounting flange 1074 that supports the encoder unit 1070 which is mounted to an encoder slide 1072 that is in a fixed position relative to the cam follower plate 1022 whose position is determined by the position of the 3D cylindrical cam (not shown). Also shown in this embodiment of the fruit testing machine 1000 is the second riser assembly which includes a fruit paddle 1016 that couples to the transducer unit 1012 which is supported on the top of the sampling arm 1008 and a vertical riser 1018.

In related embodiments, the encoder slide 1072 is mounted to the riser encoder mounting flange 1074 in a position enabling it to sense the absolute and/or relative position of the cam follower plate 1022 to which the one or plurality of riser assemblies (such as the second riser assembly 1018 and its corresponding components as illustrated 1008, 1012 and 1016). In one embodiment, the encoder unit 1070 operates to measure the relative linear displacement of the encoder unit relative to a fixed or relative position relating to said encoder unit or prior position of said encoder unit.

In one embodiment of the disclosure, the fruit testing machine 1000 features an encoder assembly top plate 1062 and/or an encoder assembly side plate, either of which may operate to hold and support said encoder unit 1070 or a component thereof, and which may also operate to protect and shield the components of the encoder assembly as disclosed. In one embodiment, the riser encoder mounting flange 1074 is fixedly attached to the cam follower plate 1022, with the encoder unit 1070 fixedly attached to the encoder assembly side plate 1064, which may optionally be attached to the encoder assembly top plate 1062, if present, the side plate 1064 providing a fixed reference point for the encoder unit 1070, which is capable of determining the relative or absolute position of the encoder unit 1070 with respect to the position of the cam follower plate 1022. In related embodiments, the encoder unit and encoder slide may be mounted on other fixed reference points and moving reference points associated with or communicating with said cam follower plate 1022, respectively, so that either an absolute or relative position of the latter plate can be determined as desired. In one embodiment of the invention, positional data transmitted by the encoder unit 1070 is received by a controller module (not shown) of the instant inventive device for the purpose of monitoring the relative position of the cam follower plate 1022, and by inference, the relative positions of other components of the inventive device with respect to the cam follower plate 1022. In further embodiments of the invention, the data provided by the encoder unit 1070 may be used to control or trigger the beginning of a measurement cycle by the fruit testing machine 1000, and/or to trigger the start of data recordation from the one or plurality of transducer units 1012 or other instrumentation present on one or more of the sampling arms 1008.

In related embodiments of the disclosure, the encoder unit is any suitable device or means of determining an absolute or relative position with respect to a standard position or starting position, and which is capable of measuring or determining a relative linear displacement of the cam follower plate 1022, or alternatively one or a plurality of the sampling arms 1008 with sufficient accuracy as needed. Suitable devices include linear and rotational encoders, the latter suitable in configurations that enable them to sense and measure a rotational position, being either an absolute or relative position with respect to a standard position or starting position, and which is capable of measuring or determining a relative angular displacement of the 3D cylindrical rotary cam with sufficient accuracy as needed. In operation, the encoder unit operates to produce a measurement and corresponding electrical signal indicative of the relative position of one or more components of the fruit testing machine 1000 as disclosed in the embodiments thereof discussed in relation to the preceding figures and description.

Figure 11:
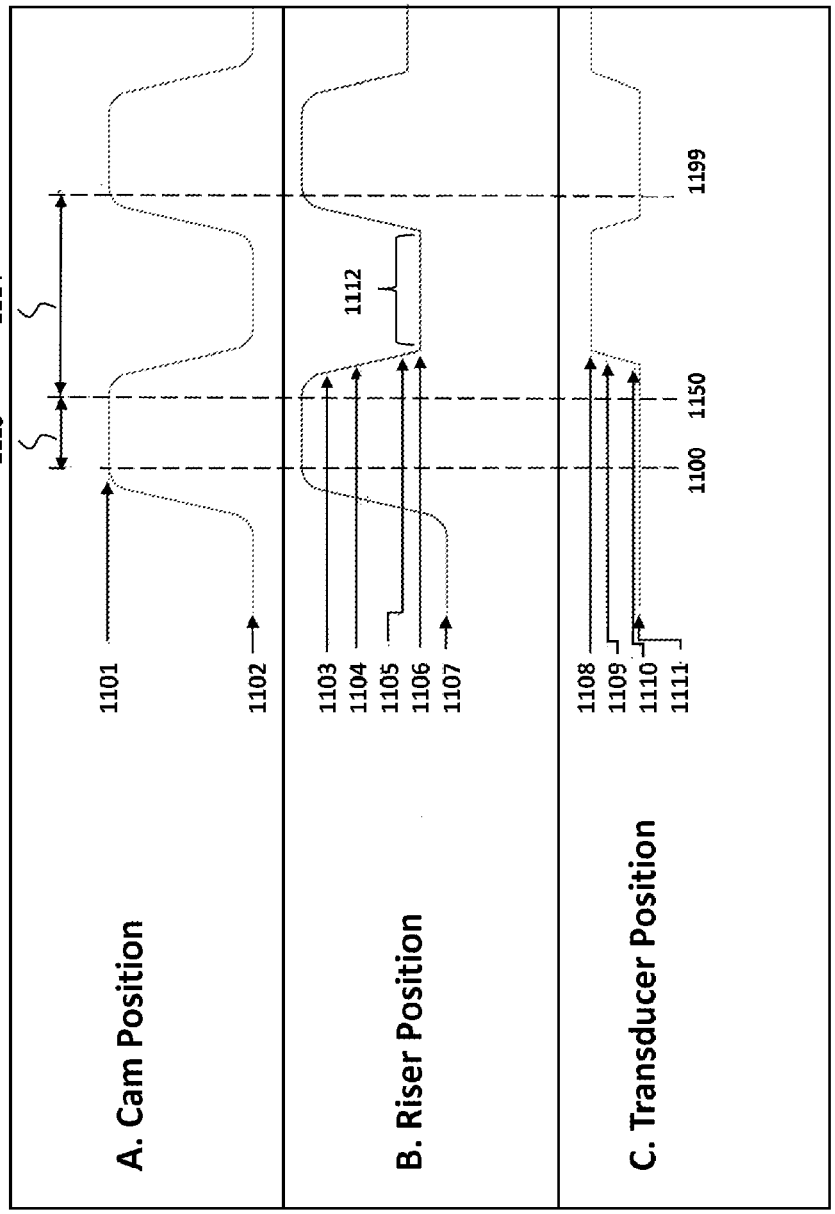
FIG. 11 shows an illustration of the relative positions in one embodiment of a fruit testing machine of the cam, riser assembly and transducer assemblies as a function of Geneva wheel rotation representing one complete text cycle.

FIG. 11 shows an illustration of the relative positions in one embodiment of a fruit testing machine of the cam, riser and transducer assemblies as a function of (cycle) time with respect to the Geneva wheel rotation representing one complete test cycle. In the embodiment shown in FIG. 11, the upper most trace A illustrates the relative position of the 3D cylindrical rotary cam with respect to the starting cam position or lowermost position corresponding to the bottom of the cam range 1102, and moving as a function of (cycle) time (rotation of said cam) to an uppermost position or top of cam range 1101, at the start of the preparation stage 1113 of the inventive device. In this embodiment of the disclosure, the preparation stage 1113 begins with the cam at the top of the cam range 1101, at which point in the cycle all risers are positioned at the top position of their range of motion as well, ensuring that the risers and their components, such as the paddle and transducer (or other measurement device or instrumentation) are raised sufficiently above the top surface of the turntable so as not to interfere or touch any test objects or fruit pieces present at sampling wells on the surface of said turntable, corresponding to the start of a full cycle 1100, a full cycle being defined here as one completion of a preparation stage 1113, measurement stage 1114, and an intermediate indexing stage 1112. In one embodiment, the measurement stage 1114 begins with all risers positioned at the top position of their range, as indicated by Trace B which shows the riser positions to be at a maximum during the preparation stage 1113 so that all risers are at their highest or most vertical top of range position at the beginning of the measurement stage 1150. At this point in the cycle, the continued rotation of the 3D cylindrical cam of the inventive device in this embodiment operates to start lowering the one or plurality of riser assemblies by means of the cam follower associated with the 3D cylindrical cam which lowers the common riser slide to which all riser assemblies are attached, but capable of independent vertical movement when not supported by the common riser slide, so that each individual riser assembly can decouple itself from the lowering of the riser slide when that individual riser assembly's fruit paddle makes actual contact with a test object of fruit piece located below and within its range of vertical descent. Accordingly, in this and related embodiments, the riser assemblies each descend freely, independently of one another, and after the first contact with a test object or fruit piece that interrupts their descent, then continue to descend freely acting solely by means of the riser assembly's own weight to continue to compress the test object or fruit piece. Put in other terms, embodiments of the inventive device employ a controlled free fall means to lower the fruit paddle or other sensing element into contact with the test object/fruit piece to be measured, and then acts to decouple any further downward movement or movement due to compression of the test object from the continuing downward motion of the common riser slide, so that from the point of contact with the test object/fruit piece, each individual riser assembly moves on its own accord as determined by its weight (mass) and the movement (i.e. compression or deformation) of the test object or fruit piece. Accordingly, in the embodiment illustrated in FIG. 11, the common riser plate and all associated riser assemblies each start at its uppermost position as point in the cycle where the measuring stage begins 1150, and then are lowered while in a supported mode by the common riser plate until the first contact between the paddle and fruit 1103 occurs. At this stage, that particular riser assembly and its respective paddle are then supported by the resistance to compression by the test object or fruit with which contact has been made. As the common riser plate continues to be lowered, the riser assembly, owing to its own weight being no longer supported by the common riser plate, then acts to compress and/or deform the fruit piece to a greater extent as more and more of the free weight of the riser assembly continues to bear down on the test object fruit piece. At the starting point or point of first contact between the paddle and fruit 1103, the test object or fruit piece experiences a combined compression force (weight) of about 500 g (grams). In other embodiments, a weight can be added to the riser assembly to adjust this weight from about 50 g to about 5000 g, as desired, and depending on the total desired weight of the riser assembly which depends on the nature of the test object or fruit piece and the desired degree of compression or distortion needed in order to complete an acceptable measuring cycle. Naturally, in embodiments using the inventive device to test cherries, a smaller weight of between 100 to 750 g can be employed, or alternatively between 150 to 600 g, or alternatively between 250 to 500 g, can be added to the riser assembly to achieve the desired degree of compression or travel range needed.

In related embodiments measuring other fruit pieces like apples, for example, a larger weight of between 500 to 5,000 g, or alternatively between 750 to 3,500 g, or alternatively between 1,000 to 2,500 g, or yet alternatively between 1,500 to 2,000 g can be added to the riser assembly to achieve the desired degree of compression or travel range needed to measure a more resilient and less compressible fruit piece or test object compared to a cherry. In other embodiments of the invention, the riser assemblies can be adjusted in height so that when the common riser plate and cam position are at their maximum vertical height or position, the respective paddles, transducer element or sensing elements located on the bottom of the sampling arm do not touch or interfere with the test object or fruit piece to be tested.

Regarding FIG. 11, as the cam position continues to change (Trace A), the riser position shown in Trace B continues to descend beyond the point of first paddle/fruit contact 1103 with an initial supported weight owing to still being supported by the descending common riser plate, so that the paddle operates to subject the test object/fruit piece to an initial net force of 0 (zero) grams at first contact, followed by an incrementally increasing weight/force of approximately 50 g at point 1104, at which stage the fruit piece is partially compressed owing to the continued support of the riser assembly by the common riser plate. As the common riser plate continues to descend after first contact of the fruit paddle, the fruit piece is compressed to a greater extent, experiencing a total increased weight/force of approximately 350 g at position 1105, which for a cherry fruit piece denotes the end of the useful measuring stage as compression beyond this point is irreversible owing to interior structural damage to the fruit post testing. In the embodiments of the invention disclosed here and related embodiments, the selection of the weights to be used to adjust the weight of the riser assemblies is selected to be sufficient so as to compress the fruit piece through the first reversible resilient compression stage of a fruit onward through a second irreversible non-resilient compression stage. In other embodiments, the inventive device can be used to test other objects that do not exhibit either a first reversible resilient compression stage, and/or a second irreversible non-resilient compression stage, or combination thereof that are more commonly associated with objects that can be compressed to a point without irreversible distortion or damage but which are distorted or damaged irreversibly if compressed beyond said prior first compression stage.

In the embodiment shown in FIG. 11, the descending common riser plate eventually decouples fully from the riser assembly, so that the riser position is at its lowest point, corresponding approximately to position 1106 when the riser is essentially "floating" or fully supported only by the test object or fruit piece itself, here subjecting the fruit piece to the full weight of 500 g. In most embodiments, measurements stop at this stage corresponding to position 1106 when the riser is essentially floating or fully supported only by the test object or fruit piece, because at this point the desired data has been collected, and with respect to compression data, the object has been fully compressed by the weight and no useful addition data readings are desired. In embodiments of the invention in which a resilient object is being tested that does not have a point of irreversible damage, continued measurement up to this maximum compression point (or lowest travel position of the riser assembly and its associated sensors) and beyond as the common riser plate begins to rise and re-engage and support the individual riser assemblies, can be incrementally or continuously obtained, as the object decompresses owing to the lessening weight it is subject to, as the weighted riser assemblies move upward towards their initial top of range position. In other embodiments in which a test object is tested to destruction or some intermediate point of maximum force, continued measurement up to some desired maximum weight or force can be done and then measurement activity discontinued or ignored.

In the embodiment shown in FIG. 11, trace C shows the transducer position, at least initially with respect to all riser assemblies, beginning at the highest point of travel of the riser(s) at the top of riser position, which corresponds to the position during the preparation stage 1113, and the top of the cam range 1101. As the 3D cylindrical rotary cam rotates and changes its rotational position, the cam follower tracks the rotation and the instant position of the grooved cam surface and communicates that position via the cam follower shaft which then communicates that position to one or a plurality of riser encoder slides, whose positions vertically change from an initial low position to an intermediate top position in concert with the rotational movement of the 3D cylindrical rotary cam from a first start position in which the cam follower is at its highest position and an intermediate second position after completing at least one full revolution upon its axis, wherein the cam follower is at its lowest position. During this period of the measuring stage 1114, the riser position decreases as discussed above, being lowered by the descending common riser plate, until the point of first contact of paddle/fruit at point 1103, corresponding to the beginning of collectable test data from the transducer whose paddle has just made contact with the test object/fruit piece indicated by point 1111, at which point in the cycle that the paddle has just engaged with the fruit piece and is still supported by the descending common riser plate so that the fruit piece is subject (through the paddle) to an instant compression force of zero (0) g at this instance. In this embodiment, as the cam position and riser positions continue to lower, the riser assembly continues to exert greater and greater force (weight) on the test object/fruit piece reaching an intermediate point 1110 at which the fruit is being subject to about 50 g of force (weight) and then to a second intermediate point 1109 at which the fruit is being subject to about 350 g of force. Further lowering of the riser assembly results in complete disengagement from the common riser plate, resulting in that riser assembly now "floating" free and thus acting to exert its full force (weight) onto the test object/fruit piece, denoted in Trace C as point 1108, at which point the transducer position is at its lowest position relative to the surface of the turntable and fully engaged with the full weight of its associated riser assembly being brought to bear upon the test object/fruit piece. The key advantage of this measurement approach is that the test object or fruit piece is subject only to a smooth, gravitational force as exerted by the partially supported riser assemblies of the present disclosure.

During this period of time (cycle) corresponding to the start of the measuring stage at point 1114 to approximately the start of the indexing stage 1112, the corresponding transducer(s) or other sensor elements associated with the riser assembly may record or take measurements or interrogate the test sample/fruit piece in a manner consistent to the operation of the sensor element. For embodiments of the disclosure wherein the sensor element is a transducer or other similar force measuring device employed for compression testing, the point of time (cycle) at which the test object/fruit piece is subject to the full weight of the riser assembly is generally a point at which no further measurements are needed, corresponding to the start the indexing stage 1112. In this and related embodiments, the cam position, riser position and associated sensor (transducer) positions are changing during the indexing stage 1112 to reset the instant inventive testing device for another cycle of testing, to begin at point 1119 for a second or repeated test cycle start, corresponding to the beginning of the first cycle start 1100 where the cam position is at the top of the cam range 1101.

In the embodiment described in FIG. 11, the measuring stage 1114 includes a measurement period that typically ends at the start of the indexing stage 1112, and the indexing stage 1112, at which point in the cycle the inventive device is in a configuration that has advanced the turntable one well position counterclockwise (or clockwise) to the next test position in embodiments with one testing station, or alternatively has advanced the turntable two well positions counterclockwise (or clockwise) to place either the next single or next set of two test objects/fruit pieces in position for testing. Accordingly, in the embodiments of the inventive device disclosed, the 3D cylindrical cam position changes and essentially repositions the inventive device into a configuration nearly identical to that at the beginning of the next testing cycle start 1100, with the exception that the turntable has been rotated the requisite number of wells so as to advance the next test sample/fruit piece or plurality (set) of next test samples/fruit pieces. In further embodiments of the disclosure, the test cycle is repeated until every test object/fruit piece present in sample wells has been subject to a testing cycle.

In further embodiments, the end of an individual test cycle for one or a set of test objects preferentially results in the 3D cylindrical cam returning to its top of range position and the positions of the corresponding sampling arms and risers also being at the top of range position so as to enable the movement of the Geneva gear and associated mechanisms to index the turntable to a new position corresponding to the next test cycle while providing sufficient clearance so that the turntable can be rotated without the test objects/fruit pieces contacting any part of the device, risers, paddles or other components prior to the commencement of the next test cycle. In related embodiments of the disclosure, the inventive device indexes to the start of the next suitable test position corresponding to the start of a new cycle 1199 following the completion of a previous cycle starting at point 1101.

In further embodiments, the end of a complete series of test cycles for all of the test objects/fruit pieces preferentially results in the 3D cylindrical cam returning to its top of range position and the positions of the corresponding sampling arms and risers also being at the top of range position so as to enable the loading and unloading of test objects/fruit pieces onto and from the top surface of the turntable, respectively.

Figure 12:
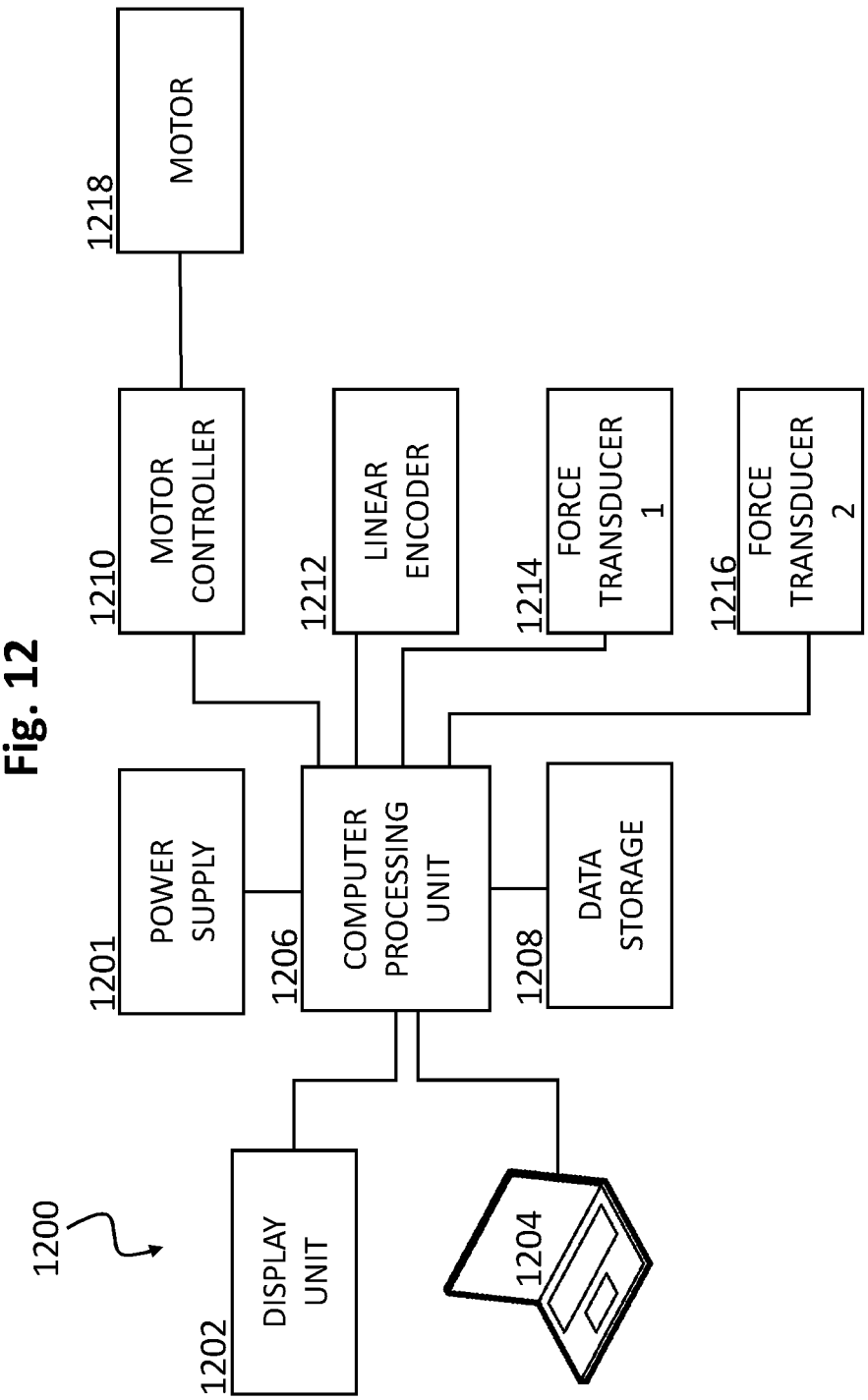
FIG. 12 shows a block diagrammatic representation of one embodiment of a fruit testing machine control module and the corresponding electronic, computer and mechanical units thereof.

FIG. 12 shows a diagrammatic representation or schematic block diagram of one embodiment of a control module 1200 suitable for controlling the electronic and mechanical components of the instant invention. The control module 1200 draws power from a power supply 1201 which powers a computer processing unit 1206 or CPU, which has attached peripherals including a display unit 1202 which displays data and system information to the user including test results, and an input unit 1204 which operates to allow a user to interface with the CPU by means of manual input via a keyboard, mouse, touch pad, reactive touch screen, voice command and the like. In one embodiment of the invention, the CPU 1206 operates to control the other units and modules by means of sending electronic and digital signals, commands and communications common to modules connected to the CPU, including the display unit 1202, the data storage unit 1208, the motor controller 1210 and the motor 1218. In a related embodiment of the invention, the CPU 1206 operates to receive and process electronic and digital signals, commands and communications transmitted by selected modules including the input unit 1204, the linear encoder 1212, a first force transducer 1214, and an optional second force transducer 1216. In one embodiment of the invention, the first and second force transducers, 1214 and 1216, independently record the force exerted against a first and second test object located at a first and second test position or well on the turntable, being the measured force or resistance to compression by the object subject to the weight of the respective first and second sampling arm and riser assembly bearing down upon the objects as the riser position is lowered so as to bring the sensors and/or paddles into contact with the first and second test objects. Once the measuring cycle is completed, the CPU 1206 operates to index the turntable to a new set of test positions while raising the sampling arms connected to the risers, by means of using the motor and optional motor controller to drive the rotation of the Geneva turntable indexing wheel and the three dimensional cylindrical cam to positions corresponding to the start of a subsequent test cycle, and further operates to raise the risers to a sampling position and then enable them to be lowered onto the second set of test objects to be measured, the cycle repeated until all sets of test objects have been subjected to testing, and the corresponding data signals obtained from the plurality of transducers received, recorded and analyzed to provide compressibility data or profiles of each separate test object measured.

In other embodiments of the invention, the various components, units and control modules of the instant invention can be interconnected in any acceptable configuration that enables a user to interface with the inventive device to initiate measurements of one or a plurality of test objects, subject the objects to a test procedure, communicate the results of that test procedure back to a user by some means common to the art including a digital or analog signal, data or visual representation thereof, and optionally store the results thus obtained for later review and/or subsequent analysis.

Motor

While a DC motor has been exampled herein as a suitable means for motive force to drive the 3D cylindrical cam and associated Geneva wheel mechanism, other embodiments of the instant invention may employ an AC motor, hydraulic motor or pneumatic motor to power the mechanical motion. Suitable alternating current (AC) motors include synchronous motors, stepper motors, asynchronous motors, induction motors, single & three phase motors, varied structure motors, and the like. Suitable direct current (DC) motors also include permanent-magnet motors, stator motors, series motors, shunt motors, cumulative compound motors, brushless motors, and the like. Further, in other embodiments, the motor may be selected from hydraulic motor, pneumatic motor and the like.

It is noted that the use of a stepper or incremental motor to power the embodiments of the instant invention is also suitable since the motor operates the mechanisms of the machine rather than being used to apply the compressive force onto the test object. And further, although the motor operates to raise and lower the riser and test stations into contact with the test object, the test stations become decoupled from the riser at the instant of contacting the test object, so that resulting compressibility data is not superimposed with incremental force artifacts from a stepper or incremental motor, because the overall compression forces acting on the test object is then due to gravitational force, i.e. the weight of the sampling arm.

Geneva Drive Mechanism

The Geneva drive mechanism consists of a Geneva drive pulley that is connected by some suitable means to the gear motor pulley for motive force to drive the rotation of the Geneva drive mechanism, which interfaces with the Geneva drive pin via a series of cutouts or indents located on the outer peripheral surface of the Geneva turntable indexing wheel. The indents are configured and spaced so that the Geneva drive mechanism is coupled by the gear motor pulley when it is desired to drive the rotation of the turntable to the next position corresponding to a second or subsequent test cycle of a new set of objects; and the indents are also configured and spaced so that the Geneva drive mechanism becomes decoupled from the gear motor pulley when it is desired that the turntable remains in a stationary position while the gear motor operates to drive the rotation of the three dimensional cam and the cam follower assembly and associated risers to position them between a top of cam range and a bottom of cam range for the purpose of initiating a new test measurement cycle.

Accordingly, in one embodiment of the invention, the number and position of the indents on the outer periphery of the Geneva turntable indexing wheel are selected depending on the number of sample wells desired, and positioned adjacently and in a selected quantity corresponding to the number of testing stations and corresponding risers that are present, the total number of indents corresponding to the total number of sets of sampling wells present. For example, if sixteen (16) wells are present on the turntable in one embodiment of the invention, there will be a corresponding number of eight (8) Geneva drive indents and eight (8) Geneva blocking stop indents, the former acting to allow the Geneva pulley to index the Geneva turntable indexing wheel while the movement of the three dimensional cam is prevented by the Geneva blocking disc, and the latter acting to prevent rotation of the Geneva turntable indexing wheel while the three dimensional cam is rotationally indexed.

With respect to the types of test objects that may be tested using the inventive device, any compressible object is suitable for use, as well as any compressible fruits, vegetables, seed, nuts, and the like, without limit, provided that the object is a least partially compressible to an extent capable of providing a detectable signal for measurement by any one embodiment of the invention as disclosed herein.

The above illustration provides many different embodiments or embodiments for implementing different features of the invention. Specific embodiments of components and processes are described to help clarify the invention. These are, of course, merely embodiments and are not intended to limit the invention from that described in the claims.

Although the invention is illustrated and described herein as embodied in one or more specific examples, it is nevertheless not intended to be limited to the details shown, since various modifications and structural changes may be made therein without departing from the spirit of the invention and within the scope and range of equivalents of the claims. Accordingly, it is appropriate that the appended claims be construed broadly and in a manner consistent with the scope of the invention, as set forth in the following claims.

What is claimed is:

1. A device for measuring a compressibility characteristic of a test object comprising:
    (a) at least one gravity assisted measuring station comprising:
        (i) a riser;
        (ii) a sampling arm associated with said riser;
        (iii) at least one sensor element associated with said sampling arm;
        (iv) a paddle associated with said sensor element;
        wherein said sampling arm is attached to said riser in a manner that enables said sampling arm to move vertically upward in synchronicity with an upward movement of said riser;
        wherein said sampling arm is attached to said riser in a manner that enables said sampling arm to decouple its downward movement from a downward vertical movement of said riser following an instance of first contact of said sensor element or said paddle with a test object to be measured by said sensor element;
    (b) a turntable;
        wherein said turntable is rotationally indexable with respect to the position of said measuring station; and
    (c) a drive mechanism which operates to index said turntable to a position corresponding to said measuring station and which operates to raise and lower said riser during a measurement operation.

2. The device of claim 1, further comprising a power supply, a computer processing unit, an input unit, a display unit, a motor, at least one linear encoder, a first and second sensor element;
    wherein said input and display units are selected from a cathode ray tube (CRT) computer, laptop, tablet computing device, digital or analog display unit, cellular communications device and combinations thereof;
    wherein said first and second sensor elements generate electronic signals that are received and analyzed by said computer processing unit;
    wherein said computer processing unit controls said motor and said motor control unit to raise and lower said first and second sampling arms and to rotate said turntable for the purpose of measuring a compressibility characteristic of test objects located within sampling wells on an upper surface of said turntable; and
    wherein said computer processing unit controls the indexing of said turntable by means of said motor controller unit between a first testing position and a subsequent second testing position whereby a compression test of a first set and subsequent additional set of test objects can be completed automatically without user intervention after a loading step of said plurality of test objects into said plurality of sampling wells has been completed prior to starting said compression test.

3. The device of claim 1, wherein said riser comprises:
    (i) a unit slide that operates to raise and lower said sampling arm associated with said riser; wherein an upper portion of said sampling arm supports at least one sensor element oriented in a downward sensing position; wherein said sampling arm is attached to an upper portion of said unit slide; and wherein a lower portion of said unit slide is connected to a cam follower assembly;
    (ii) a cam follower assembly attached to a lower portion of said unit slide; wherein said cam follower assembly operates to raise and lower said unit slide; wherein said cam follower assembly raises said unit slide in a first upward vertical direction to a maximum height corresponding to a top of cam position and then further operates to lower said unit slide in a second downward vertical direction to an intermediate measuring position corresponding to a test position that operates to bring said sensor element into contact with a test object positioned on said turntable in order to measure said compressibility characteristic of said test object, and then further operates to allow said paddle associated with said sensor element to compress said test object by means of gravitational force until said unit slide achieves a lowermost final position as determined by a degree of compression of said test object as measured between an initial uncompressed state and a final compressed state.

4. The device of claim 3, wherein said cam follower assembly comprises:
    (i) a cam follower plate that is attached to a lower portion of one or a plurality of said risers;
    (ii) a cam follower; and
    (iii) a cam follower shaft; wherein said cam follower has a proximal side that is attached to said cam follower plate and an opposite distal side that is attached to said cam follower shaft;
    wherein said cam follower operates to convert the rotational motion of a three dimensional cylindrical cam into a linear vertical motion with a first maximum vertical position corresponding to said top of cam position and to a second intermediate lower vertical position corresponding to said start of test position sequentially during one rotation of said three dimensional cylindrical cam;
    wherein said three dimensional cylindrical cam has a grooved cam surface featuring a continuous cam channel located on the three dimensional cylindrical cam's outer surface of rotation that couples with said cam follower;

wherein said cam follower is attached to the can follower shaft and guides said cam follower shaft during rotation of the three dimensional cylindrical cam about a vertically oriented axis of rotation of said three dimensional cylindrical cam.

5. The device of claim 4, wherein said turntable has a plurality of shallow sample wells located on the upper surface of said turntable;

wherein said sample wells are each configured to receive and hold one test object in a stationary position with respect to said sample well; and wherein said sample wells are positioned radially equidistant about the center axis of rotation of said turntable; and wherein said turntable is rotationally indexable and operates to position at least one test object held within a sample well under at least on measuring station.

6. The device of claim 5, further comprising a second measuring station comprising a second riser, a second sampling arm, a second sensor element and a second paddle associated with said second sensor element;

wherein said turntable is rotationally indexable and operates to position at least two separate test objects held within at least two adjacent sample wells, a first sample well and a second sample well, in alignment with said first and said second measuring station, respectively, prior to a measurement operation.

7. The device of claim 5, wherein said drive mechanism operates to drive the rotation of a Geneva turntable indexing wheel that comprises a plurality of Geneva drive indents and a plurality of Geneva blocking stop indents; wherein said Geneva drive indents are configured to engage a Geneva driving pin located on the Geneva drive pulley that operates to rotationally index said turntable between a loading position and a first measuring position; wherein said loading position is selected from a position located immediately adjacent to said first measuring position located under a first measuring station; and wherein said first measuring position corresponds to a first set of one or plurality of positions that correspond to positions of sample wells located on the surface of said turntable with test objects present that are aligned with and located immediately under one or a plurality of measuring stations when said turntable is rotated into said first measuring position; wherein said Geneva drive indents are configured so as to decouple from said Geneva driving pin and prevent the further rotation of said turntable during a first measurement cycle; and wherein said Geneva drive indents further operate to engage said Geneva driving pin to index said turntable to a second and subsequent plurality of measuring positions wherein an additional one or plurality of test objects present are then subsequently aligned with and located immediately under said measuring stations during said second and said subsequent measurement operations.

8. The device of claim 7, wherein said Geneva driving pin on said Geneva drive pulley is configured to engage with a first Geneva drive indent at a first position and which operates to rotationally index said turntable to a second position whereby the Geneva driving pin decouples from said first Geneva drive indent, and remains decoupled until said Geneva drive pulley is rotated to a third position whereby the Geneva driving pin couples with a second and adjacent Geneva drive indent, corresponding to the end of a first measurement operation; and wherein said Geneva driving pulley operates to rotate said three dimensional cylindrical cam one complete rotation about its axis during any one of said measurement operations; wherein said three dimensional cylindrical cam operates to drive said cam follower along said cam follower groove located on said grooved cam surface of said three dimensional cylindrical cam.

9. The device of claim 8 wherein said drive mechanism is a motor selected from an electronic motor, DC motor, AC motor, synchronous motor, gear motor, stepper motor, and combinations thereof.

10. The device of claim 8 wherein an upper surface of said three dimensional cylindrical cam is axially connected to and operates to rotate in synchronicity with said Geneva drive pulley;

wherein said Geneva drive pulley is coupled to a gear motor pulley by a suitable mechanical linkage that enables said gear motor to turn said Geneva drive pulley; and wherein said mechanical linkage is selected from a ball chain, belt, link chain, clutch, wire, gear system, slip clutch, and combinations thereof.

11. The device of claim 10, wherein said three dimensional cylindrical cam is axially connected to said Geneva drive pulley by means of keyed drive shaft whose proximal end is supported by a set of upper drive shaft bearings and whose distal end is supported by a set of lower drive shaft bearings; and wherein said upper and lower drive shaft bearings and said gear motor are contained within a drive bearing housing.

12. The device of claim 11, wherein said proximal end of said keyed drive shaft couples to the lower engagement surface of said Geneva drive pulley that bears said Geneva driving pin on an opposite or upper engagement surface of said Geneva drive pulley;

wherein said Geneva driving pin extends upwardly and into the plane of rotation of the Geneva turntable indexing wheel and operates to engage with said Geneva drive indents located on the outer peripheral edge of said Geneva turntable indexing wheel; and which further operates to couple with said Geneva turntable indexing wheel when said Geneva drive pulley is in a position corresponding to any one of a plurality of rotational positions corresponding to the start of a measurement operation; and wherein said Geneva drive pulley operates to rotate said three dimensional cam which in turn operates to raise and lower one or a plurality of said risers bearing said sampling arms.

13. The device of claim 10, wherein said one or a plurality of sampling arms further comprises a sensor unit connected to said sampling arm and oriented in a downward direction for sensing compressive forces exerted by said sampling arm against a test object located within a sample well and positioned in coaxial alignment with said test object located within said sample well on said surface of said turntable; wherein said sensor unit bears a paddle on its lowermost surface wherein said paddle has a contact surface that operates to contact said test object and further operates to distribute the weight of said sampling arm uniformly across said contact surface of said paddle when in contact with said test object; wherein said paddle operates to transmit said compressive forces between said test object and said sensor unit.

14. The device of claim 7, wherein said drive mechanism drives the rotation of a Geneva blocking disc; wherein said drive mechanism is coupled to said Geneva turntable indexing wheel by means of said Geneva drive pulley driven by a keyed drive shaft;

wherein said Geneva blocking disc mates with said Geneva blocking stop indents when they are brought into rotational alignment and which operates to prevent the rotation of said turntable during any one of said measurement operations; and wherein said Geneva blocking disc is located at a proximal end of said keyed drive shaft and is in a plane coincident to a plane passing through the Geneva turntable indexing wheel and perpendicular to a vertical axis passing through the long axis of said keyed drive shaft.

15. The device of claim 4, wherein said first and second riser comprise a first unit slide and a second unit slide;

wherein said first and second unit slide are connected on their respective lower ends to the proximal side of a first slide carriage plate and a second slide carriage plate, respectively; and wherein said first and second slide carriage plates are coupled on their distal sides to a proximal side of said cam follower plate;

wherein said cam follower plate bears said cam follower shaft on it distal side.

16. The device of claim 15, wherein the distal side of said cam follower plate is connected to an encoder slide assembly; wherein said encoder slide assembly comprises an encoder assembly top plate, an encoder assembly side plate to which said encoder unit is attached; and a riser encoder mounting flange that connects to said cam follower plate to provide a reference vertical displacement scale against which the instantaneous vertical position of said encoder slide can be measured; wherein said encoder slide assembly consists of an encoder slide carriage, an encoder slide and an encoder mount block; wherein said encoder slide operates to travel vertically within the encoder slide carriage when vertically driven by said cam follower plate; and wherein a linear encoder is mounted to one side of said encoder mount block and operates to generate an electronic signal that is proportional to the instantaneous vertical position of said linear encoder with respect to its subsequent vertical displacement from an initial set position corresponding to said bottom of cam range.

17. The device of claim 16, wherein said first and said second risers operate to travel vertically within a first unit slide and a second unit slide, respectively, driven vertically by means of said cam follower plate;

wherein said first and second unit slides bear a plurality of slide vee rollers that engage with a plurality of slide vee guides located within said respective unit slide grooves of said first and second unit slides;

wherein said slide vee rollers engage said slide vee guides to enable the vertical movement of said risers from a lowermost vertical position defined as said bottom of cam range to an uppermost vertical position defined as said top of cam range; and wherein a set of first and second slide mount limit screws located at the bottom of their respective first and second unit slides and which operate to arrest any further downward vertical movement of said first and second unit slides beyond the lowermost vertical position corresponding to said bottom of cam range.

18. A device for measuring a compressibility characteristic of a test object comprising:

(a) a gravity assisted measuring station comprising:
  (i) a riser;
  (ii) a sampling arm associated with said riser;
  (iii) a sensor element associated with said sampling arm;
  (iv) a paddle associated with said sensor element;
(b) a turntable having a plurality of shallow sample wells located on an upper surface of said turntable;
wherein said sample wells are each configured to receive and hold one test object in a stationary position with respect to said sample well; and wherein said sample wells are positioned radially equidistant about a center axis of rotation of said turntable; and
wherein said turntable is rotationally indexable and operates to position at least one test object held within a sample well under at least on measuring station;
(c) a drive mechanism
wherein said sampling arm is attached to said riser in a manner that enables said sampling arm to move vertically upward in synchronicity with an upward movement of said riser;
wherein said sampling arm is attached to said riser in a manner that enables said sampling arm to decouple its downward movement from a downward vertical movement of said riser following an instance of first contact of said sensor element or said paddle with a test object to be measured by said sensor element;
wherein said turntable is rotationally indexable with respect to the position of said measuring station;
wherein said drive mechanism operates to index said turntable to a position corresponding to said measuring station and which operates to raise and lower said riser during a measurement operation;
wherein said riser consists of (i) a unit slide and (ii) a cam follower assembly;
wherein said unit slide operates to raise and lower said sampling arm associated with said riser; wherein an upper portion of said sampling arm supports at least one sensor element oriented in a downward sensing position; wherein said sampling arm is attached to an upper portion of said unit slide; wherein a lower portion of said unit slide is connected to a cam follower assembly; wherein said cam follower assembly is attached to a lower portion of said unit slide and operates to raise and lower said unit slide; wherein said cam follower assembly raises said unit slide in a first upward vertical direction to a maximum height corresponding to a top of cam position and then further operates to lower said unit slide in a second downward vertical direction to an intermediate measuring position corresponding to a test position that operates to bring said sensor element into contact with a test object positioned on said turntable in order to measure said compressibility characteristic of said test object, and then further operates to allow said paddle associated with said sensor element to compress said test object by means of gravitational force until said unit slide achieves a lowermost final position as determined by a degree of compression of said test object as measured between an initial uncompressed state and a final compressed state;
wherein said cam follower assembly consists of (i) a cam follower plate that is attached to a lower portion of one or a plurality of said risers; (ii) a cam follower; and (iii) a cam follower shaft; wherein said cam follower has a proximal side that is attached to said cam follower plate and an opposite distal side that is attached to said cam follower shaft;

wherein said cam follower operates to convert the rotational motion of a three dimensional cylindrical cam into a linear vertical motion with a first maximum vertical position corresponding to said top of cam position and to a second intermediate lower vertical position corresponding to said start of test position sequentially during one rotation of said three dimensional cylindrical cam;

wherein said three dimensional cylindrical cam has a grooved cam surface featuring a continuous cam channel located on said three dimensional cylindrical cam's outer surface of rotation that couples with said cam follower; wherein said cam follower is attached to the can follower shaft and guides said cam follower shaft during rotation of the three dimensional cylindrical cam about a vertically oriented axis of rotation of said three dimensional cylindrical cam; and wherein said drive mechanism operates to drive the rotation of a Geneva turntable indexing wheel that comprises a plurality of Geneva drive indents and a plurality of Geneva blocking stop indents; wherein said Geneva drive indents are configured to engage a Geneva driving pin located on the Geneva drive pulley that operates to rotationally index said turntable between a loading position and a first measuring position; wherein said loading position is selected from a position located immediately adjacent to said first measuring position located under a first measuring station; and wherein said first measuring position corresponds to a first set of one or plurality of positions that correspond to positions of sample wells located on an upper surface of said turntable with test objects present that are aligned with and located immediately under one or a plurality of measuring stations when said turntable is rotated into said first measuring position; wherein said Geneva drive indents are configured so as to decouple from said Geneva driving pin and prevent a further rotation of said turntable during a first measurement cycle; and wherein said Geneva drive indents further operate to engage said Geneva driving pin to index said turntable to a second and subsequent plurality of measuring positions wherein an additional one or plurality of test objects present are then subsequently aligned with and located immediately under said measuring stations during said second and said subsequent measurement operations; wherein said Geneva driving pin on said Geneva drive pulley is configured to engage with a first Geneva drive indent at a first position and which operates to rotationally index said turntable to a second position whereby the Geneva driving pin decouples from said first Geneva drive indent, and remains decoupled until said Geneva drive pulley is rotated to a third position whereby the Geneva driving pin couples with a second and adjacent Geneva drive indent, corresponding to an end of a first measurement operation; and wherein said Geneva driving pulley operates to rotate said three dimensional cylindrical cam one complete rotation about its axis during any one of said measurement operations; wherein said three dimensional cylindrical cam operates to drive said cam follower along said cam follower groove located on said grooved cam surface of said three dimensional cylindrical cam; wherein said drive mechanism drives a rotation of a Geneva blocking disc; wherein said drive mechanism is coupled to said Geneva turntable indexing wheel by means of said Geneva drive pulley driven by a keyed drive shaft;

wherein said Geneva blocking disc mates with said Geneva blocking stop indents when they are brought into rotational alignment and which operates to prevent a rotation of said turntable during any one of said measurement operations; and wherein said Geneva blocking disc is located at the proximal end of said keyed drive shaft and is in a plane coincident to a plane passing through the Geneva turntable indexing wheel and perpendicular to a vertical axis passing through the long axis of said keyed drive shaft.

19. A method for measuring a compressibility characteristic of one or more test objects in a repeated series of steps defining a complete test cycle using a device comprising:
(a) at least one gravity assisted measuring station comprising:
  (i) a riser;
  (ii) a sampling arm associated with said riser;
  (iii) at least one sensor element associated with said sampling arm;
  (iv) a paddle associated with said sensor element;
wherein said sampling arm is attached to said riser in a manner that enables said sampling arm to move upward in synchronicity with an upward movement of said riser; and
wherein said sampling arm is attached to said riser in a manner that enables the sampling arm to decouple its downward movement from a downward movement of said riser following an instance of first contact of said sensor element or said paddle with said test object to be measured by said sensor element;
(b) a turntable; wherein said turntable has a plurality of sample wells and is rotationally indexable with respect to a position of said measuring station; and
(c) a drive mechanism which operates to index said turntable to a position corresponding to said measuring station and which operates to raise and lower said riser;
wherein said steps comprise:
  (A) enabling said drive mechanism to simultaneously raise said sampling arm to permit a loading of test objects to be measured in a first and subsequent plurality of sets of said sample wells located on an upper surface of said turntable;
  (B) enabling said drive mechanism to then lower said sampling arm by means of said risers in order to bring said sensor element with attached paddle into contact with a first test object for the purpose of measuring a degree of compression of a said first test object independently in a first measurement operation;
  (C) collecting electronic data generated by said sensor element during said first measurement operation;
  (D) enabling said drive mechanism to simultaneous raise said sampling arm and to rotationally index said turntable to a subsequent test position wherein a new test object in a second sample wells are located under said sampling arm;
  (E) repeating steps B, C and D in this order for each unmeasured test object to be tested, and repeating these steps until the last test object has been measured in a final measurement operation representing the end of a complete test cycle; and
  (F) enabling said drive mechanism to raise said sampling arm and rotationally index said turntable to a final position wherein all the test objects can be removed from their respective sample wells on said turntable.

20. The method of claim 19, wherein said device further comprises a power supply, a computer processing unit, an input unit, a display unit, a motor, at least one linear encoder, a first and second sensor elements; and a motor controller unit and data storage unit;

wherein said linear encoder provides an output corresponding to an instantaneous relative vertical position of said linear encoder with respect to a first and second position of said first and second sampling arms and their respective first and second sensor elements during each testing operation so as to enable a compression force applied to each test object to be independently measured and recorded during a test cycle of a plurality of differently sized test objects each located on its own sample well on a surface of said turntable.

* * * * *